US012594265B2

(12) United States Patent
Yang et al.

(10) Patent No.: US 12,594,265 B2
(45) **Date of Patent: *Apr. 7, 2026**

(54) METHODS AND COMPOSITIONS FOR INHIBITION OF STAT3

(71) Applicant: Ohio State Innovation Foundation, Columbus, OH (US)

(72) Inventors: Yuhong Yang, Dublin, OH (US); Chenglong Li, Gainesville, FL (US); Michael Racke, Powell, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 747 days.

This patent is subject to a terminal disclaimer.

(21) Appl. No.: 17/821,286

(22) Filed: Aug. 22, 2022

(65) Prior Publication Data

US 2023/0103257 A1 Mar. 30, 2023

Related U.S. Application Data

(63) Continuation-in-part of application No. 16/650,494, filed as application No. PCT/US2018/053085 on Sep. 27, 2018, now Pat. No. 11,420,946.

(60) Provisional application No. 62/563,849, filed on Sep. 27, 2017.

(51) Int. Cl.
*A61K 31/428* (2006.01)
*A61K 31/18* (2006.01)

(52) U.S. Cl.
CPC ............ *A61K 31/428* (2013.01); *A61K 31/18* (2013.01)

(58) Field of Classification Search
CPC .............................. A61K 31/18; C07D 275/06
See application file for complete search history.

(56) References Cited

U.S. PATENT DOCUMENTS

| | | | |
|---|---|---|---|
| 2012/0040924 | A1 | 2/2012 | Cho et al. |
| 2013/0085180 | A1 | 4/2013 | Clement et al. |
| 2015/0166484 | A1 | 6/2015 | Daniels et al. |

FOREIGN PATENT DOCUMENTS

| | | | |
|---|---|---|---|
| WO | 20110066263 | | 6/2011 |
| WO | WO2011066263 | A1 | 6/2011 |
| WO | 20120097351 | | 7/2012 |
| WO | WO2012097351 | | 7/2012 |
| WO | 2014028909 | A | 2/2014 |
| WO | WO2014028909 | | 2/2014 |

OTHER PUBLICATIONS

Lin et al. "A Novel Small Molecule, LLL12, Inhibits STAT3 Phosphorylation and Activities and Exhibits Potent Growth-Suppressive Activity in Human Cancer Cells" NEOPLASIA vol. 12 No. 1. Jan. 2010. pp. 39-50.

Nie et al. "A novel small inhibitor, LLL12, targets STAT3 in non-small cell lung cancer in vitro and in vivo" 1Department of Gastrointestinal Medical Oncology, Hubei Province Cancer Hospital; 2College of Chemistry, Central China Normal University, Wuhan, Hubei 430079, P.R. China. 2018 DOI: 10.3892/ol.2018.9262.

Kroon et al. "JAK-STAT Blockade Inhibits Tumor Initiation and Clonogenic Recovery of Prostate Cancer Stem-like Cells" Cancer Res; 73(16) Aug. 15, 2013.

Lin et al. "A small molecule, LLL 12 inhibits constitutive STAT3 and IL-6-induced STAT3 signaling and exhibits potent growth suppressive activity in human multiple myeloma cells" Int. J. Cancer: 130, 1459-1469 (2012).

Zuo et al. "LLL12, a novel small inhibitor targeting STAT3 for hepatocellular carcinoma therapy" Oncotarget, vol. 6, No. 13. 2015 pp. 10940-10949. www.impactjournals.com/oncotarget.

Bid HK, Oswald D, Li C, London CA, Lin J, et al. (2012) Anti-Angiogenic Activity of a Small Molecule STAT3 Inhibitor LLL12. PLoS One 7(4): e35513.doi:10.1371/journal.pone.0035513.

Ball S, Li C, Li P-K, Lin J (2011) The Small Molecule, LLL12, Inhibits STAT3 Phosphorylation and Induces Apoptosis in Medulloblastoma and Glioblastoma Cells. PLoS One 6(4): e18820. doi:10.1371/journal.pone.0018820.

Lin et al. "STAT3 as a potential therapeutic target in ALDH+ and CD44+/CD24+ stem cell-like pancreatic cancer cells" International Journal of Oncology 49: 2265-2274, 2016. DOI: 10.3892/ijo.2016.3728.

Zhang et al. "A small molecule STAT3 inhibitor, LLL12, enhances cisplatinand paclitaxel-mediated inhibition of cell growth" Oncology Reports 4 1224 4: 1224-1232, 2020. DOI: 10.3892/pr.2020.7667.

Andrea L.A. Wong, Jayshree L. Hirpara, Shazib Pervaiz, Jie-Qing Eu, Gautam Sethi & Boon-Cher Goh (2017) Do STAT3 inhibitors have potential in the future for cancer therapy?, Expert Opinion on Investigational Drugs, 26:8, 883-887, DOI: 10.1080/13543784.2017.1351941.

Chun et al. "Alantolactone selectively suppresses STAT3 activation and exhibits potent anticancer activity in MDA-MB-231 cells" http://dx.doi.org/10.1016/j.canlet.2014.11.049.

Hubbard et al. "Napabucasin: An Update on the First-in-Class Cancer Stemness Inhibitor" Springer International Publishing Switzerland 2017. Drugs (2017) 77:1091-1103. DOI 10.1007/s40265-017-0759-4.

Wang et al. "Suppression of the Growth and Invasion of Human Head and Neck Squamous Cell Carcinomas via Regulating STAT3 Signaling and the miR-21/b-catenin Axis with HJC0152" Mol Cancer Ther 2017;16:578-590. Published Online First Jan. 30, 2017. American Association for Cancer Research. DOI: 10.1158/1535-7163.MCT-16-0606.

(Continued)

*Primary Examiner* — Shawquia Jackson
(74) *Attorney, Agent, or Firm* — Thomas | Horstemeyer , LLP

(57) ABSTRACT

In one aspect, the disclosure relates to prodrug compositions of a STAT inhibitor compound. In some aspects, the STAT is STAT3. Disclosed are pharmaceutical compositions comprising the prodrug inhibitors of STAT. In various aspects, the prodrug inhibitors of STAT can be used in methods of treating an inflammatory disorder, including multiple sclerosis, or a disorder of uncontrolled cellular proliferation, such as a cancer. This abstract is intended as a scanning tool for purposes of searching in the particular art and is not intended to be limiting of the present disclosure.

19 Claims, 20 Drawing Sheets

(56) References Cited

OTHER PUBLICATIONS

Bharadwaj et al. "Small-molecule inhibition of STAT3 in radioresistant head and neck squamous cell carcinoma" Oncotarget, vol. 7, No. 18 (2016) www.impactjournals.com/oncotarget. pp. 26307-26330.
Wong et al. "Phase I and biomarker study of OPB-51602, a novel signal transducer and activator of transcription (STAT) 3 inhibitor, in patients with refractory solid malignancies" Annals of Oncology 26: 998-1005, 2015. doi:10.1093/annonc/mdv026 Published by Oxford University Press on behalf of the European Society for Medical Oncology.
Furtek et al. "Strategies and Approaches of Targeting STAT3 for Cancer Treatment" ACS Chem. Biol. 2016, 11, 308-318. DOI: 10.1021/acschembio.5b00945.
Bosch-Barrera et al. "Silibinin and STAT3: A natural way of targeting transcription factors for cancer therapy" Cancer Treatment Reviews 41 (2015) 540-546. http://dx.doi.org/10.1016/j.ctrv.2015.04.008.
EP Search Report mailed May 28, 2021 for EP Application No. 18860926.7.
Attarha Sanaz et al: "Validating Signal Transducer and Activator of Transcription (STAT) Protein-Inhibitor Interactions Using Biochemical and Cellular Thermal Shift Assays", ACS Chemical Biology, vol. 15, No. 7, May 15, 2020 (May 15, 2020), pp. 1842-1851.
International Search Report issued for PCT/US2018/053085, mailed Nov. 20, 2018.
Lin et al., A Novel Small Molecule, LLL12, Inhibits STAT3 Phosphorylation and Activities and Exhibits Potent Growth-Suppressive Activity in Human Cancer Cells, Neoplasia, 12(1), p. 39-50, 2010.
Lala, P K, and A Orucevic. "Role of nitric oxide in tumor progression: lessons from experimental tumors." Cancer and Metastasis Reviews ( 1998), 17 ( 1), 91-106.
Golub, T R et al. "Molecular classification of cancer: class discovery and class prediction by gene expression monitoring." Science (New York, N.Y.) vol. 286,5439(1999), vol. 286, 531-537. doi:10.1126/science.286.5439.531.
Cancer [online], [retrieved on Jul. 6, 2007]. Retrieved from the internet, URL http://www.nlm.nih.gov/medlineplus/cancer.html>.
Attarha Sanaz et al: "Validating Signal Transducer and Activator of Transcription (STAT) Protein-Inhibitor Interactions Using Biochemical and Cellular Thermal Shift Assays", ACS Chemical Biology, vol. 15, No. 7, May 15, 2020 (May 15, 2020), pp. 1842-1851, XP055803568, ISSN: 1554-8929, DOI: 10.1021 /acschembio.0c00046.
European Office Action for EP Application 18860926.7 mailed Nov. 11, 2024 .

LLL12
Parent Molecule
LLL12a
Prodrug Molecule
LLL12c
Prodrug Molecule
LLL12b
Prodrug Molecule

LLL12B

LLL12Ba

LLL12Bd1

LLL12Bad1

LLL12Bd2

LLL12Bad2

LLL12Bd3

LLL12Bd4

LLL12Bd5

LLL12Bd6

LLL12Bd7

LLL12Bd8

LLL12Bd9

LLL12Bd10

METHODS AND COMPOSITIONS FOR INHIBITION OF STAT3

CROSS-REFERENCE TO RELATED APPLICATIONS

This application is a continuation-in part of U.S. Non-provisional application Ser. No. 16/650,494, filed Mar. 25, 2020, which is a National Stage of International Application No. PCT/US2018/053085, filed Sep. 27, 2018, which claims the benefit of U.S. Provisional Application No. 62/563,849, filed on Sep. 27, 2017, each of which is incorporated herein by reference in its entirety.

STATEMENT REGARDING FEDERALLY SPONSORED RESEARCH

This disclosure was made with U.S. Government support under grant number 1R01NS088437-01A1 awarded by the National Institute of Neurological Disorders and Stroke (NINDS) of the National Institutes of Health. The U.S. government has certain rights in the disclosure.

BACKGROUND

IL-6 is an important cytokine that contributes to host defense against pathogens and IL-6/STAT3 signaling pathway plays a central role in regulating T effector/T regulatory (Teff/Treg) balance (1, 2). Teff/Treg balance is critical for the normal function of the immune system and impaired balance leads to either autoimmunity or increased susceptibility to foreign pathogens. IL-6/STAT3 pathway has recently been identified as the key cytokine-signaling pathway regulating Teff/Treg balance. First, IL-6, signaling through STAT3, induces the development of highly encephalitogenic myelin-specific Th17 cells. IL-6 differentiates naïve CD4 T cells into IL-17 producing Th17 cells, transferring severe disease in the experimental autoimmune encephalomyelitis (EAE) model of MS (3), (4, 5). Furthermore, IL-23, the cytokine crucial for the expansion of encephalitogenic myelin-specific Th17 cells in vivo and is required for EAE development (6-11), signals through STAT3 (12-15).

Thus. STAT3 is a common transcription factor regulating the development of encephalitogenic myelin-specific CD4 T cells by transducing signals from two inflammatory cytokines, IL-6 and IL-23 (FIG. 2). Via a positive feedback loop, IL-6 enhances expression and/or activation of IL-6 itself, IL-17 and STAT3 and vise versa (16, 17). Meanwhile, IL-6/STAT3 pathway is also a keysignaling pathway blocking the development of inducible T regulatory cells (iTreg), which is critical for dampening pathogenic inflammatory T effector responses. IL-6, signaling through STAT3, completely abrogates the de novo induction of iTreg cells (18, 19). As a result, dysregulated IL-6/STAT3 signaling skews Teff/Treg balance toward an enhanced T effector response, favoring the development of autoimmunity. In addition, IL-6/STAT3 signaling contributes to the resistance of Teff cells to Treg-mediated suppression (20, 21), which further impairs Teff/Treg balance, leading to increased susceptibility to autoimmunity.

Dysregulation of IL-6 signaling plays a significant role in the pathogenesis of MS and other autoimmune disease. IL-6 message and protein levels were elevated in the central nervous system (CNS) of MS patients (22, 23) and B cells from MS patients secret significantly more IL-6 than healthy controls (HC) (24). Furthermore, CD4 T cells from MS patients have significantly more IL-6 receptors (IL-6R) than HC (25) and the expression of phosphorylated STAT3 (pSTAT3) in peripheral blood mononuclear cells (PBMC) from relapsing-remitting MS (RRMS) patients strongly correlates with MS disease activity (26). T effector cells from active RRMS patients, but not HC, are resistant to Treg suppression and impaired Treg suppression correlates with an increase expression of IL-6R□ and pSTAT3. When STAT3 phosphorylation was blocked, the impaired suppression was reversed (20). All these data demonstrated a dysregulated IL-6/STAT3 signaling pathway in MS patients. Thus, IL-6/STAT3 signaling pathway may serve as an innovative target for reversing pathogenesis in MS patients. In support of this strategy, IL-6−/−, IL-23−/− and STAT3−/− mice are all completely resistant to EAE induction (10, 27-31), while injection of recombinant IL-6 induces severe EAE in IL-6−/− mice (28).

Moreover, constitutive activation of STAT3 has been found in a wide variety of cancers, including breast cancer, sarcomas, and other cancers, promoting it as a very attractive therapeutic target. Cytokines, hormones, and growth factors binding to the cell surface receptors can activate the JAK-STAT signaling pathway. The receptors are activated and phosphorylated by JAK kinase(s). Subsequently, the STAT3 monomer is phosphorylated at Tyrosine705 (pTyr705) by the same kinases through its SH2 domain binding to pY loop of the activated receptors, leading to STAT3 homodimer through its SH2 dimerization. The dimerized STAT3 then translocates into the nucleus and binds to DNA, turning on a host of oncogenes. Altogether, these events such as cell proliferation and apoptosis resistance.

Despite advances in developing therapeutic intervention targeting function of the IL6/STAT3 signalling pathway, there is still a scarcity of compounds that are both potent, efficacious, and safe inhibitors of IL6/STAT3 dysregulation during disease states and pathogenesis. These needs and other needs are satisfied by the present disclosure.

SUMMARY

In accordance with the purpose(s) of the disclosure, as embodied and broadly described herein, the disclosure, in one aspect, relates to prodrug compositions of a STAT inhibitor compound. In some aspects, the STAT is STAT3. Disclosed are pharmaceutical compositions comprising the prodrug inhibitors of STAT. In various aspects, the prodrug inhibitors of STAT can be used in methods of treating an inflammatory disorder, including multiple sclerosis, or a disorder of uncontrolled cellular proliferation, such as a cancer.

Disclosed are compounds having a structure represented by a formula:

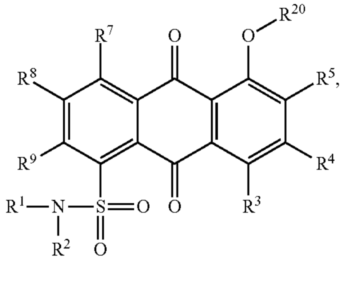

wherein each of $R^1$ and $R^2$ is independently selected from hydrogen and C1-C6 alkyl; wherein each of $R^3$, $R^4$, R5, $R^7$, $R^8$, and $R^9$ is independently selected from hydrogen, C1-C6 alkyl, C1-C6 alkoxy, halogen, —$NO_2$, —$NH_2$, and —OH; and wherein $R^{20}$ is —C(O)—O—(C1-C6 alkylene), —C(O)—(C1-C6 alkylene), —C(O)—(C1-C6 alkylene)-C(O)OH, —C(O)—$NR^{21}R^{22}$, and —(C1-C6 alkylene)-$PO_3H_2$; wherein each of $R^{21}$ and $R^{22}$ is independently selected from hydrogen and C1-C6 alkyl; or a pharmaceutically acceptable salt thereof.

Also disclosed are pharmaceutical composition comprising a therapeutically effective amount of a disclosed compound, or a pharmaceutically acceptable salt, thereof, and a pharmaceutically acceptable carrier.

Also disclosed are methods for the treatment of an inflammatory disorder in a mammal comprising the step of administering to the mammal a therapeutically effective amount of at least one disclosed compound, or a pharmaceutically acceptable salt, thereof, or a disclosed pharmaceutical composition.

Also disclosed are methods for the treatment of a disorder of uncontrolled cellular proliferation in a mammal comprising the step of administering to the mammal administering a therapeutically effective amount of at least one disclosed compound, or a pharmaceutically acceptable salt, thereof, or a disclosed pharmaceutical composition.

Also disclosed are methods for inhibiting STAT activity in a mammal comprising the step of administering to the mammal administering a therapeutically effective amount of at least one disclosed compound, or a pharmaceutically acceptable salt, thereof, or a disclosed pharmaceutical composition.

Also disclosed are methods for inhibiting STAT activity in at least one cell, comprising the step of contacting the at least one cell with an effective amount of at least one disclosed compound, or a pharmaceutically acceptable salt, thereof, or a disclosed pharmaceutical composition.

Also disclosed are kits comprising at least one disclosed compound, or a pharmaceutically acceptable salt, thereof, or a disclosed pharmaceutical composition; and one or more of: at least one agent known to increase STAT activity; at least one agent known to decrease STAT activity; at least one agent known to treat a inflammatory disorder; at least one agent known to treat a disease of uncontrolled cellular proliferation; instructions for treating a disorder associated with a STAT dysfunction; instructions for treating an inflammatory disorder; or instructions for treating a disease of uncontrolled cellular proliferation.

Also disclosed are uses of a disclosed compound, a disclosed product of making, or a pharmaceutically acceptable salt thereof.

Also disclosed are uses of a disclosed compound, a disclosed product of making, or a pharmaceutically acceptable salt thereof, in the manufacture of a medicament for the treatment of a disorder associated with a STAT dysfunction in a mammal.

Also disclosed are methods for the manufacture of a medicament to inhibit a STAT protein in a mammal comprising combining at least one disclosed compound, a disclosed product of making, or a pharmaceutically acceptable salt thereof with a pharmaceutically acceptable carrier or diluent.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

FIG. 3A shows intracellular flow cytometric data obtained from cells gated on live CD4+CD44+ cells that were either not exposed to LLL12 (DMSO control, first panel) or to increasing concentrations of LLL12 (second panel to fifth panel). FIG. 36 shows IL17 production data as determined by ELISA analysis of supernatants from the cells used in the analysis for FIG. 3A.

FIG. 5A shows intracellular flow cytometric data obtained from cells gated on live CD4+CD44+ cells that were not exposed to drug (DMSO-treated control cells). FIG. 5B shows intracellular flow cytometric data obtained from cells gated on live CD4+CD44+ cells that were exposed to 0.25 μM LLL12b. FIG. 5C shows intracellular flow cytometric data obtained from cells gated on live CD4+CD44+ cells that were exposed to 0.25 μM LLL12c.

FIG. 7A shows representative data on the IL-17 production in myelin-specific CD4 T cells that were not treated with a disclosed compound (DMSO control treatment) compared to the indicated concentrations of treatment with LLL12b. The data were obtained by intracellular flow cytometric analysis. The data show a dose-dependent inhibition of IL-17 production in these cells. FIG. 7B shows representative data on the pSTAT3 levels in myelin-specific CD4 T cells under the indicated conditions (MBP Ac1-1 activation, MBP Ac1-1 and IL-6 activation with DMSO control treatment, and MBP Ac1-1 and IL-6 activation with 0.25 μM LLL12b treatment). The data were obtained by intracellular flow cytometric analysis. The data show LLL12b-dependent inhibition of pSTAT3 levels in these cells.

FIG. 8A shows presentative mean clinical score data from a representative experiment out three independent experiments. The data show a statistically significant suppression in the mean clinical score reflecting the suppression of EAE development in animals treated with LLL12b. FIG. 8B shows data for IL-17 production determined using ELISA for samples from splenocytes isolated from mice that had been treated with DMSO or LLL12b, and then activated with MOG 35-5 for 3 days. The data show decreased production of IL-17 in animals that had been treated with LLL12b.

FIG. 9A shows presentative mean clinical score data from a representative experiment out of four independent experiments in which splenocytes from naïve TCR transgenic mice were activated with MBP Ac1-11 plus IL-6 for 3 days, and then injected into naïve B10PL mice. The mice were then treated with either DMSO or a representative disclosed compound, LLL12b, (10 mg/kg) by daily intraperitoneal for 7 days. FIG. 9B shows representative peak clinical scores comparing results obtained from the DMSO and LLL12b treatment groups. FIG. 9C shows area under the curve comparing results obtained from the DMSO and LLL12b treatment groups.

FIG. 10A shows data for intracellular flow cytometric analysis of CD25+FoxP3+CD4+ Treg cells. FIG. 10B shows Treg population summary data for each treatment group. FIG. 10C shows data from splenocytes obtained from the LLL12b- or DMSO-treated group as indicated which were activated with MBP Ac1-11 for 3 days followed by determination of IFNγ production by ELISA. The data show a statistically significant increase in the level of Treg cells in LLL12b-treated animals. Moreover, the data show a notable decrease in the production of IFNγ.

FIG. 11A shows the effect of daily injection (days 9-15) of either LLL12b (10 mg/kg) or DMSO as indicated on mean clinical score. During the treatment period, more than half of the mice showed clinical signs of EAE. FIG. 11B shows the effect of daily injection (days 36-42) of either LLL12b (10 mg/kg) or DMSO as indicated on mean clinical score. During the treatment period, EAE mice were in remitting phase. The data show a statistically significant beneficial effect of LL12b treatment on clinical scores in both the acute and remitting phases in this model.

FIG. 12A shows the effect on IL-17 production under the indicated conditions as determined by ELISA. FIG. 12B shows the effect on IFNγ production under the indicated conditions as determined by ELISA.

FIG. 13A shows a representative flow plot of pSTAT3 in DMSO treated cells from one MS patient. FIG. 13B shows a representative flow plot of pSTAT3 in LLL12b treated cells from one MS patient. FIG. 13C shows representative data for pSTAT3 status in LLL12b treated and DMSO treated groups from 6 treatment-naïve MS patients summarized and compared with Wilcoxon matched-pairs signed rank test for significance ($P<0.05$). * denotes $P<0.05$.

FIGS. 14A, 14E, 14H, and 14K each shown representative data obtained in PBMCs from 22 treatment-naïve MS patients that were activated with αhCD3 plus rhIL-6 for 3 days, in the presence of 0.125 μM or 0.25 μM of LLL12b. DMSO was used as a vehicle control. IL-17 in supernatant was determined by ELISA. FIGS. 14B-14C, 14F, 14I, and 14L each shown representative data obtained in PBMCs from 22 treatment-naïve MS patients that were activated with αhCD3/CD28 plus rhTGFβ. rhIL-2 and RA for 3 days, in the presence of 0.125 μM of LLL12b. DMSO was used as vehicle control. CD25+FoxP3+CD4+ iTregs were determined by intracellular flow cytometry. Cells were gated CD45RA+CD4+ cells. FIG. 14A shows representative IL-17 ELISA data of one MS patient. IL-17 in each group was compared with one-way ANOVA. FIG. 14B shows a representative flow plot of CD25+FoxP3+CD45RA+CD4+ iTregs in a DMSO treated group from one MS patient. FIG. 14C shows a representative flow plot of CD25+FoxP3+ CD45RA+CD4+ iTregs in an LLL12b treated group from one MS patient. FIG. 14D shows the results obtained from a non-parametric Pearson correlation test was used to analyze the degree of relatedness between the percent increase of iTreg and the percent decrease of IL-17. FIG. 14E shows data for levels of IL-17 in the LLL12b (0.125 μM) treated group from 22 treatment-naïve MS patients were compared to the DMSO treated group using Wilcoxon matched-pairs signed rank test. FIG. 14F shows representative data for iTregs in LLL12b treated and DMSO treated groups from 22 treatment-naïve MS patients compared with Wilcoxon matched-pairs signed rank test. FIG. 14G the calculated IL-17/Treg ratio of each patient in LLL12b group and DMSO group and compared with Wilcoxon matched-pairs signed rank test. FIG. 14H shows representative data for the percent decrease of IL-17 production in the LLL12b treated group compared to the DMSO treated group of each patient. FIG. 14I shows the calculated percent increase of iTregs in the LLL12b treated group compared the DMSO treated group. FIG. 14J the calculated percent decrease of IL-17/Treg ratio in LLL12b group compared to DMSO group. FIG. 14K shows representative patient numbers in different ranges of percent decrease of IL-17. FIG. 14L shows representative patient numbers in different ranges of percent increase of iTregs. FIG. 14M patient numbers in different ranges of calculated percent decrease of IL-17/Treg.

FIG. 15A shows representative flow plot data for the proliferation of DMSO (upper panel) or LLL12b (lower panel) treated CD4 T cells from one MS patient at four different Teff:Treg ratios. FIG. 15B shows the calculated percent suppression by Tregs in DMSO or LLL12b treated groups at three Teff:Treg the data shown FIG. 15A. FIG. 15C shows the calculated percent suppression by Tregs in DMSO or LLL12b treated group from three MS patients (Teff:Treg=16:1) summarized and compared with a paired Student's t-test.

FIG. 16A shows representative data for IL-17 and IFNγ production in activated CD44+CD4+ T cells determined by intracellular flow staining. Cells were gated on CD44+CD4+ T cells. Flow data are representative of three independent experiments. FIG. 16B shows calculated group means compared by one-way ANOVA to the group treated with DMSO. FIG. 16C shows representative dose response curve data for the relationship of LLL12b concentration and normalized inhibition of the percentage of IL17+CD4 T cells. All error bars denote s.e.m. * * denotes $p<0.01$; * denotes $p<0.001$; ** denotes $p<0.0001$.

Figure 1:
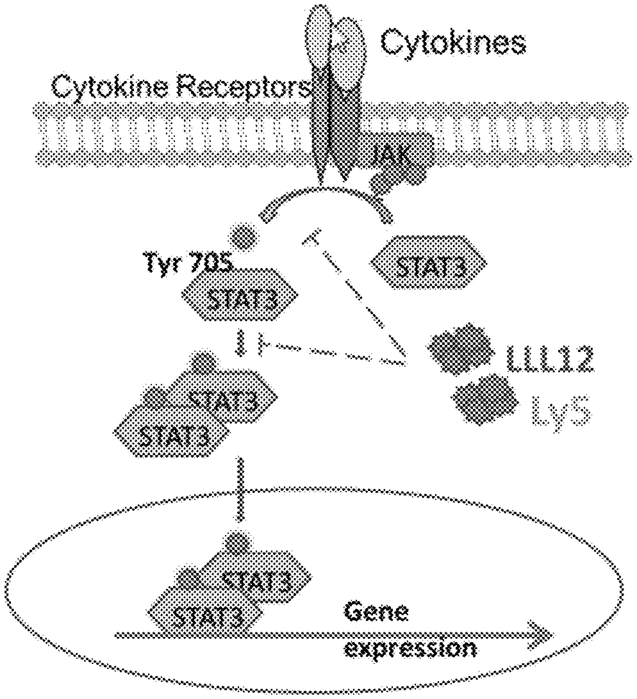
FIG. 1 shows a schematic representation of the STAT3 signalling pathway.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

Definitions

As used herein. "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of," Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate,"

"at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot °Ccur, and that the description includes instances where said event or circumstance °Ccurs and instances where it does not.

As used herein, the term "STAT" and "signal transducer and activator of transcription" can be used interchangeably, and refer to a protein family comprising at least the following members: STAT1, 2, 3, 4, 5a, 5b, and 6. The STAT family of proteins are latent cytoplasmic transcription factors that mediate cellular responses to cytokines, growth factors, and other polypeptide ligands.

As used herein, the terms "STAT3," "signal transducer and activator of transcription 3 (acute-phase response)," and "signal transducer and activator of transcription 3" can be used interchangeably and refer to a transcription factor encoded by a gene designated in human as the STAT3 gene, which has a human gene map locus of 17q21 and described by Entrez Gene cytogenetic band: 17q21.31; Ensembl cytogenetic band: 17q21.2; and, HGNC cytogenetic band: 17q21. The term STAT3 refers to a human protein that has 770 amino acids and has a molecular weight of about 88.068 Da. The term is inclusive of splice isoforms or variants, and also inclusive of that protein referred to by such alternative designations as: APRF, MGC16063, Acute-phase response factor. DNA-binding protein APRF, HIES as used by those skilled in the art to that protein encoded by human gene STAT3. The term is also inclusive of the non-human ortholog or homolog thereof.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally °Ccurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-w interactions, polar π-interactions, and hydrophobic effects.

As used herein, the term "subject" can be a vertebrate, such as a mammal, a fish, a bird, a reptile, or an amphibian. Thus, the term "subject" also includes domesticated animals (e.g., cats, dogs, rabbits, guinea pigs, etc.), livestock (e.g., cattle, horses, pigs, sheep, goats, horse, etc.), and laboratory animals (e.g., mouse, rabbit, rat, guinea pig, fruit fly, etc.). The term "subject" is also understood to include, as appropriate, a mammal such as a primate, and, in a further aspects, the subject is a human. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

In some aspects of the disclosed methods, the subject has been diagnosed with a need for treatment of one or more oncological disorders or cancers prior to the administering step. In some aspects of the disclosed method, the subject has been diagnosed with a need for inhibition or negative modulation of STAT3 prior to the administering step. In some aspects of the disclosed method, the subject has been diagnosed with a need for treatment of one or more oncological disorders or cancers associated with STAT3 dysfunction prior to the administering step.

As used herein, the terms "treating" and "treatment" can refer generally to obtaining a desired pharmacological and/or physiological effect. "Treatment" refers to the medical management of a subject with the intent to cure, ameliorate, stabilize, or prevent a disease, pathological condition, or disorder, such as an inflammatory disease, an autoimmune disease, including, but not limited to, an inflammatory disease, an autoimmune disease, including, but not limited to, multiple sclerosis, a cancer, or disease associated with a STAT3 dysfunction. The term includes active treatment, that is, treatment directed specifically toward the improvement or amelioration of a disease, pathological condition, or disorder, and also includes causal treatment, that is, treatment directed toward removal of the cause of the associated disease, pathological condition, or disorder. As used herein, and as well-understood in the art, "treatment" is an approach for obtaining beneficial or desired results, including clinical results. For purposes of the present disclosure, beneficial or desired clinical results include, but are not limited to, alleviation or amelioration of one or more symptoms, diminishment of extent of disease, stabilized (i.e., not worsening) state of disease, delay or slowing of disease progression, and/or amelioration or palliation of the disease state. "Treatment" can also mean prolonging survival as compared to expected survival if not receiving treatment.

The effect can be, but does not necessarily have to be, prophylactic in terms of preventing or partially preventing a disease, symptom or condition thereof, such as an inflammatory disease, an autoimmune disease, including, but not limited to, multiple sclerosis, a cancer, or disease associated with a STAT3 dysfunction. The effect can be therapeutic in terms of a partial or complete cure of a disease, condition, symptom or adverse effect attributed to the disease, disorder, or condition. The term "treatment" as used herein can include any treatment of an inflammatory disease, an autoimmune disease, including, but not limited to, multiple sclerosis, a cancer, or disease associated with a STAT3 dysfunction in a subject, particularly a human and can include any one or more of the following: (a) preventing the disease from °Ccurring in a subject which may be predisposed to the disease but has not yet been diagnosed as having it; (b) inhibiting the disease, i.e., arresting its development; and/or (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In some aspects of the present disclosure, reduction in the severity of one or more symptoms associated with the disease, disorder or condition can refer to amelioration of one or more of the following: pain, swelling, redness or inflammation associated with an inflammatory condition or an autoimmune disease.

As used herein, the term “prevent” or “preventing” refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, “dose,” “unit dose,” or “dosage” can refer to physically discrete units suitable for use in a subject, each unit containing a predetermined quantity of a disclosed compound and/or a pharmaceutical composition thereof calculated to produce the desired response or responses in association with its administration.

As used herein, the term “diagnosed” means having been subjected to a physical examination by a person of skill, for example, a physician, and found to have a condition that can be diagnosed or treated by the compounds, compositions, or methods disclosed herein. For example, “diagnosed with a disorder treatable by STAT3 inhibition” means having been subjected to a physical examination by a person of skill, for example, a physician, and found to have a condition that can be diagnosed or treated by a compound or composition that can inhibit or negatively modulate STAT3. As a further example. “diagnosed with a need for inhibition of STAT3” refers to having been subjected to a physical examination by a person of skill, for example, a physician, and found to have a condition characterized by a dysfunction in STAT3 activity. Such a diagnosis can be in reference to a disorder, such as an oncological disorder or disease, cancer and/or disorder of uncontrolled cellular proliferation and the like, as discussed herein. It is also understood that a diagnosis can be in reference to disorder or disease such as an inflammatory or autoimmune disorder. For example, the term “diagnosed with a need for inhibition of STAT3 activity” refers to having been subjected to a physical examination by a person of skill, for example, a physician, and found to have a condition that can be diagnosed or treated by inhibition of STAT3 activity. For example, “diagnosed with a need for modulation of STAT3 activity” means having been subjected to a physical examination by a person of skill, for example, a physician, and found to have a condition that can be diagnosed or treated by modulation of STAT3 activity, e.g. negative modulation. For example, “diagnosed with a need for treatment of one or more disorder of uncontrolled cellular proliferation associated with STAT3 dysfunction” means having been subjected to a physical examination by a person of skill, for example, a physician, and found to have one or disorders of uncontrolled cellular proliferation, e.g. a cancer, associated with STAT3 dysfunction. For example, “diagnosed with a need for treatment of one or more disorder of uncontrolled cellular proliferation associated with STAT3 dysfunction” can mean having been subjected to a physical examination by a person of skill, for example, a physician, and found to have one or disorders of inflammation or autoimmune disease, e.g., an autoimmune disease such as multiple sclerosis, associated with a STAT3 dysfunction.

“Inflammatory disorder” or “inflammatory disease” refers to a condition characterized by inflammation in a cell, tissue or body. Inflammatory diseases and disorders include, but are not limited to, atopic conditions (e.g., hypersensitivities such as allergies or asthma), autoimmune disease (e.g., rheumatoid arthritis, lupus, multiple sclerosis), cancer, diabetes, inflammatory bowel disease (IBD) or infectious disease.

As used herein, the phrase “identified to be in need of treatment for a disorder,” or the like, refers to selection of a subject based upon need for treatment of the disorder. For example, a subject can be identified as having a need for treatment of a disorder (e.g., a disorder related to STAT3 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, “therapeutic” can refer to treating, healing, and/or ameliorating a disease, disorder, condition, or side effect, or to decreasing in the rate of advancement of a disease, disorder, condition, or side effect.

As used herein, “effective amount” can refer to the amount of a disclosed compound or pharmaceutical composition provided herein that is sufficient to effect beneficial or desired biological, emotional, medical, or clinical response of a cell, tissue, system, animal, or human.

An effective amount can be administered in one or more administrations, applications, or dosages. The term can also include within its scope amounts effective to enhance or restore to substantially normal physiological function. A “therapeutically effective amount” as used herein, is intended to mean an amount sufficient to reduce by at least 10%, preferably at least 25%, more preferably at least 50%, and most preferably an amount that is sufficient to cause an improvement in one or more clinically significant symptoms in the subject.

As used herein, the term “therapeutically effective amount” refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella. Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "contacting" as used herein refers to bringing a disclosed compound and a cell, target STAT3 protein, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein, means a saturated, straight or branched hydrocarbon chain containing from 1 to 10 carbon atoms. In some instances, the number of carbon atoms in an alkyl moiety is indicated by the prefix "Cx-Cy", wherein x is the minimum and y is the maximum number of carbon atoms in the substituent. Thus, for example, "C1-C6 alkyl" refers to an alkyl substituent containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a straight or branched, saturated hydrocarbon chain, for example, of 1 to 10 carbon atoms or of 1 to 6 (C1-C6 alkylenyl) carbon atoms or of 1 to 4 carbon atoms (C1-C4 alkylenyl). Examples of alkylene and alkylenyl include, but are not limited to, —CH2-, —CH2CH2-, —CH2CH2CH2-, —CH2CH2CH2CH2-, and —CH2CH(CH3)CH2-.

The terms "alkoxy" and "alkoxyl" as used herein to refer to an alkyl or cycloalkyl group bonded through an ether linkage; that is, an "alkoxy" group can be defined as —$OA^1$ where A1 is alkyl or cycloalkyl as defined above. "Alkoxy" also includes polymers of alkoxy groups as just described; that is, an alkoxy can be a polyether such as —OA-$OA^2$ or -$OA^1$-$(OA2)_a$-$OA^3$, where "a" is an integer of from 1 to 200 and $A^1$, $A^2$, and $A^3$ are alkyl and/or cycloalkyl groups.

The term "halo" or "halogen" as used herein, means Cl, Br, I, and F.

The term "hydroxyl" or "hydroxy" means a —OH group.

The term "nitro" as used herein is represented by the formula —$NO_2$.

The term "C(O)" as used herein is a short hand notation for a carbonyl group, i.e., C=O.

The term "aldehyde" as used herein is represented by the formula —C(O)H.

The term "carboxylic acid" as used herein is represented by the formula —C(O)OH.

The moiety represented by the formula —$PO_3H_2$ has the structure represented by the following formula:

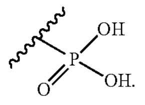 [SMILES: *P(=O)(O)O]

It is understand that the foregoing formula encompasses pharmaceutically acceptable salts thereof, such as, but not limited to, a structure represented by the following formula:

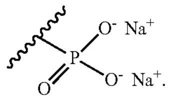

The term "ester" as used herein is represented by the formula —OC(O)$A^1$ or —C(O)$OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -$(A^1O(O)C\text{-}A^2\text{-}C(O)O)_a$— or -$(A^1O(O)C\text{-}A^2\text{-}OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500.

The term "hydroxyalkyl" as used herein, means a —OH group appended to the parent molecular moiety through an alkylenyl group, as defined herein. Non-limiting examples of hydroxyalkyl include 2-hydroxyethyl and 2-methyl-3-hydroxypropyl.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{3}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds disclosed herein can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

It is understood, that unless otherwise specified, temperatures referred to herein are based on atmospheric pressure (i.e. one atmosphere).

Disclosed herein are compounds that have therapeutic or clinical utility. Also described herein are methods of synthesizing the disclosed compounds. Also described herein are methods of administering the disclosed compounds to a subject in need thereof. In some aspects, the subject can have an inflammatory disease, an autoimmune disease, including, but not limited to, multiple sclerosis, a cancer, or disease associated with a STAT3 dysfunction. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Compounds

Disclosed herein are compounds having a structure represented by a formula:

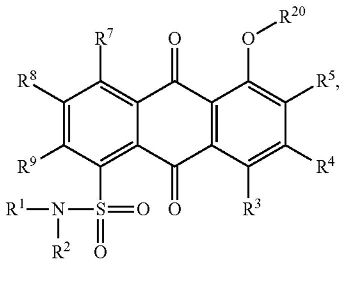

wherein each of $R^1$ and $R^2$ is independently selected from hydrogen and C1-C6 alkyl; wherein each of $R^3$, $R^4$, R5, $R^7$, $R^8$, and $R^9$ is independently selected from hydrogen, C1-C6 alkyl, C1-C6 alkoxy, halogen. —$NO_2$, —$NH_2$, and —OH; and wherein $R^{20}$ is —C(O)—O—(C1-C6 alkylene), —C(O)—(C1-C6 alkylene), —C(O)—(C1-C6 alkylene)-C(O)OH, —C(O)—$NR^{21}R^{22}$, and —(C1-C6 alkylene)-$PO_3H_2$; wherein each of $R^{21}$ and $R^{22}$ is independently selected from hydrogen and C1-C6 alkyl; or a pharmaceutically acceptable salt thereof.

In various aspects, the disclosed compound has a structure represented by a formula:

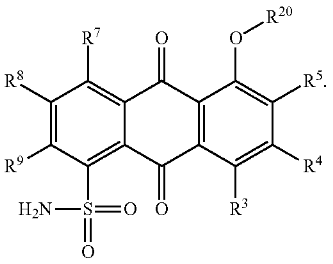

In various aspects, the disclosed compound has a structure represented by a formula:

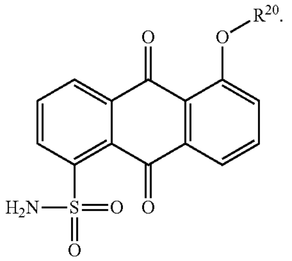

In a further aspect, $R^{20}$ can be —C(O)—(C1-C6 alkylene)-C(O)OH, —C(O)—$NR^{21}R^{22}$, and -(C1-C6 alkylene)-$PO_3H_2$; and wherein each of $R^{21}$ and $R^{22}$ is independently selected from hydrogen and C1-C6 alkyl. In a still further aspect, $R^{20}$ can be —C(O)—(C1-C6 alkylene)-C(O)OH, —C(O)—$NR^{21}R^{22}$, and -(C1-C6 alkylene)-$PO_3H_2$; and wherein each of $R^{21}$ and $R^{22}$ is independently selected from hydrogen and methyl. In a yet further aspect. $R^{20}$ can be —C(O)—$(CH_2)_2$—C(O)OH. In an even further aspect, $R^{20}$ can be C(O)—$NH_2$. In a still further aspect, $R^{20}$ can be —($CH_2$)—$PO_3H_2$.

In various aspects, the disclosed compound has a structure represented by a formula:

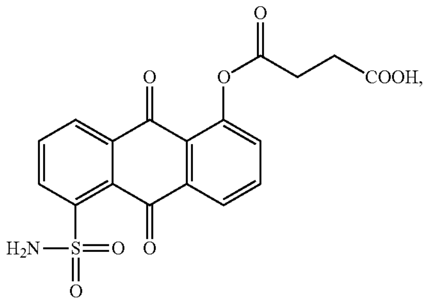

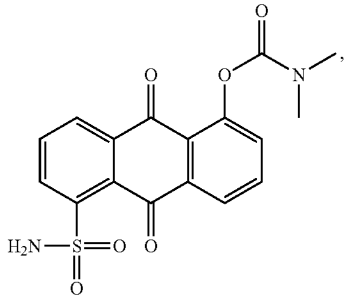

or

-continued

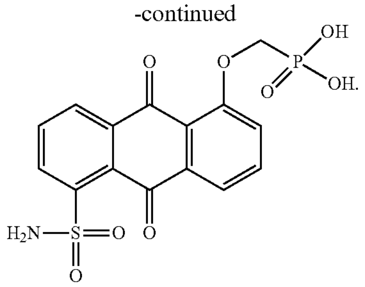

In various aspects, the disclosed compound has a structure represented by a formula:

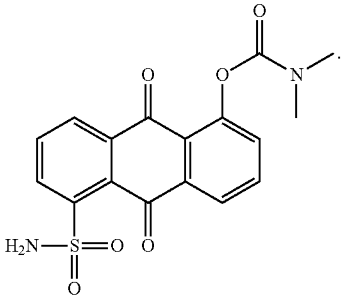 [SMILES: CN(C)C(=O)Oc1cccc2c1C(=O)c1cccc(S(N)(=O)=O)c1C2=O]

In various aspects, disclosed herein are compounds having a structure represented by a formula:

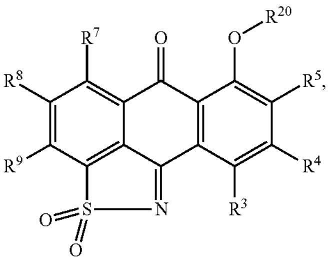

wherein each of $R^3$, $R^4$, R5, $R^7$, $R^8$, and $R^9$ is independently selected from hydrogen, C1-C6 alkyl, C1-C6 alkoxy, halogen. —$NO_2$. —$NH_2$, and —OH; and wherein $R^{20}$ is —C(O)—O—(C1-C6 alkylene), —C(O)—(C1-C6 alkylene), —C(O)—(C1-C6 alkylene)-C(O)OH, —C(O)—$NR^{21}R^{22}$, and —(C1-C6 alkylene)-$PO_3H_2$; wherein each of $R^{21}$ and $R^{22}$ is independently selected from hydrogen and C1-C6 alkyl; or a pharmaceutically acceptable salt thereof.

In a further aspect, disclosed herein are compounds having a structure represented by a formula:

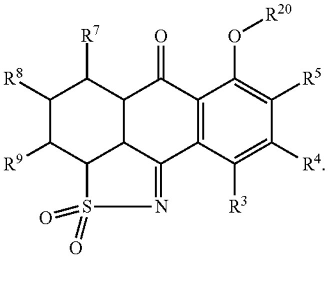

In a further aspect, disclosed herein are compounds having a structure represented by a formula:

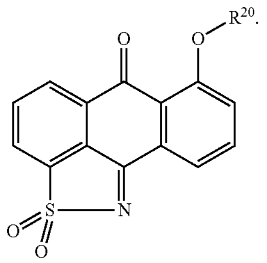

In a further aspect, disclosed herein are compounds having a structure represented by a formula:

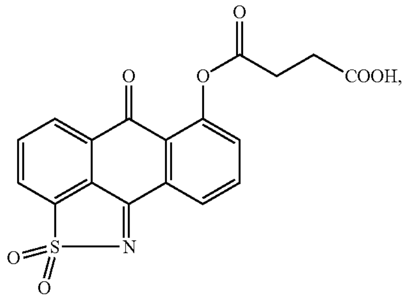

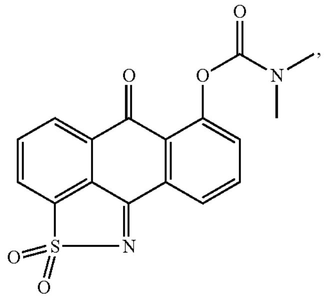

or

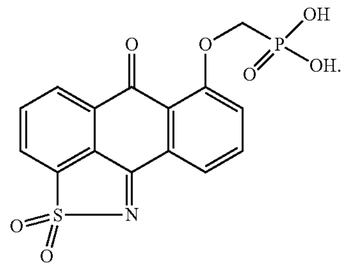

In a further aspect, disclosed herein are compounds having a structure represented by a formula:

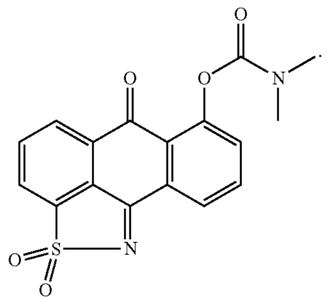 [SMILES: CN(C)C(=O)Oc1cccc2c1C(=O)c1cccc3c1C2=NS3(=O)=O]

In various aspects, it is contemplated herein that the disclosed compounds further comprise their biosteric equivalents. The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience; New York, 1970, 64-80; (ii) Burger, A.; "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", *Perspect. Drug Discovery Des.* 1998, 9/10/11, 213-224; (v) Koyanagi T, Haga T, "Bioisosterism in agrochemicals", *ACS Symp. Ser.* 1995, 584, 15-24; (vi) Kubinyi H, "Molecular similarities. Part 1. Chemical structure and biological activity". *Pharm. Unserer Zeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J. "Bioisosteric approach in the design of new dopaminergic/serotonergic ligands", *Curr. Med. Chem.* 1998, 5, 493-512 (x) Thomber C W, "Isosterism and molecular modification in drug design", *Chem. Soc. Rev.* 1979, 8, 563-80.

In further aspects, bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

In various aspects, it is contemplated herein that the disclosed compounds further comprise their isotopically-labelled or isotopically-substituted variants, i.e., compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and °Ccur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

In various aspects, the disclosed compounds can be in the form of a co-crystal. The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Preferred co-crystals include p-toluenesulfonic acid and benzenesulfonic acid.

The term "pharmaceutically acceptable co-crystal" means one that is compatible with the other ingredients of the formulation and not deleterious to the recipient thereof.

In a further aspect, the disclosed compounds can be isolated as solvates and, in particular, as hydrates of a disclosed compound, which can be obtained, for example, by crystallization from a solvent or from aqueous solution. In this connection, one, two, three or any arbitrary number of solvate or water molecules can combine with the compounds according to the invention to form solvates and hydrates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. In a further aspect, salts further include, but are not limited, to the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e., 1,1'-methylene-bis-(2-hydroxy-3-naphthoate)) salts. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia. L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Methods of Making the Compounds

In one aspect, the invention relates to methods of making compounds useful as inhibitors of STAT protein, e.g., STAT3, which can be useful in the treatment of an inflammatory disease, an autoimmune disease, including, but not limited to, multiple sclerosis, a cancer, or disease associated with a STAT3 dysfunction. In one aspect, the invention relates to the disclosed synthetic manipulations. In a further aspect, the disclosed compounds comprise the products of the synthetic methods described herein.

In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one product of the disclosed methods with a pharmaceutically acceptable carrier or diluent.

The compounds of this invention can be prepared by employing reactions as shown in the disclosed schemes, in addition to other standard manipulations that are known in the literature, exemplified in the experimental sections or clear to one skilled in the art. For clarity, examples having a fewer substituent can be shown where multiple substituents are allowed under the definitions disclosed herein. Thus, the following examples are provided so that the invention might be more fully understood, are illustrative only, and should not be construed as limiting.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

a. Synthesis Route 1

In one aspect, a useful intermediate for the preparation of the disclosed compounds of the present disclosure can be prepared generically by the synthesis scheme as shown below. All positions are defined herein.

Scheme 1A

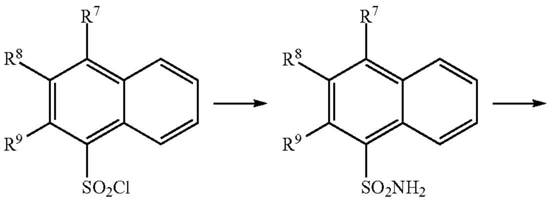

-continued

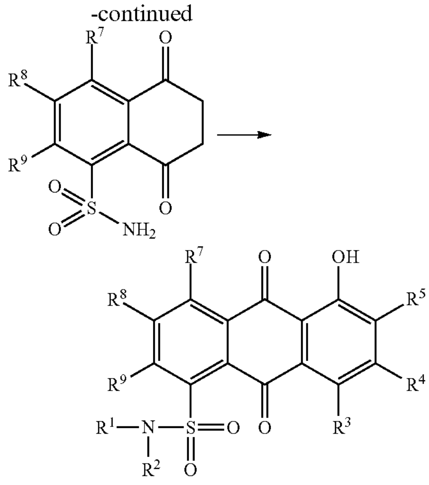

Compounds are represented in generic form, with substituents as noted in compound descriptions elsewhere herein. A more specific example is set forth below.

Scheme 1B

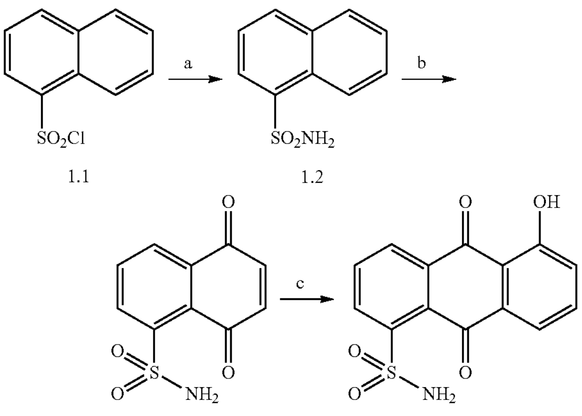

1.1 1.2 1.3 1.4 a: acetone, $NH_3 \cdot H_2O$, room temperature/3 h;
b: $Cr_2O_3$, $HOAc/H_2O$, <80° C.;
c: $CH_2Cl_2/MeOH$, $Et_3N$ (0.02 eq), 3-hydroxy-2H-pyran-2-one, -20-10° C., then room temperature/2-3 h.

A suitable substituted naphthalene-1-sulfonyl chloride analogue, e.g., compound 1.1 in reaction Scheme 1B above, and related compounds can be obtained commercially or by methods know to one skilled in the art. Thus, a suitable substituted naphthalene-1-sulfonamide analogue, e.g., a compound of type 1.2, can be prepared from compound 1.1 by a coupling reaction with a suitable amine, e.g. ammonium hydroxide as shown above. Appropriate amines are commercially available or can be prepared by methods known to one skilled in the art. The reaction is carried out at a suitable temperature, e.g. about −10-20° C., in a suitable solvent, e.g. acetone, for a period of time sufficient to complete the reaction, e.g. about 3-5 h. A suitable substituted 5,8-dioxo-5,8-dihydronaphthalene-1-sulfonamide analogue, e.g., a compound of type 1.3, can be prepared by oxidation of a compound of type 1.2. For example, as shown above, such an oxidation reaction can be accomplished using a suitable oxidizing agent, e.g. chromium trioxide, and a suitable solvent, e.g. acetone, at an appropriate temperature, e.g.

about 90-130° C., for a suitable period time, e.g. 5-30 min, before addition of a suitable protic polar solvent, e.g. water, at an appropriate temperature, e.g. −10-20° C., for a period of time sufficient to complete the reaction, e.g. about 8-16 h. A suitable substituted 5-hydroxy-9,10-dioxo-9,10-dihydroanthracene-1-sulfonamide analogue, e.g., a compound of type 1.4, can be prepared by reaction with a suitable compound, such as a substituted 3-hydroxy-1-pyrone analogue. For example, as shown above, the reaction can be carried out preparing a solution of the suitable substituted 5-hydroxy-9,10-dioxo-9,10-dihydroanthracene-1-sulfonamide analogue, e.g., a compound of type 1.4, in a suitable solvent, e.g., methylene chloride and an alcohol such as methanol, with a suitable base, such as trimethylamine, and cooling to a suitable temperature, e.g., about −50° C. to about 10° C. To the foregoing solution is added a suitable compound, a substituted 3-hydroxy-1-pyrone analogue, that is in a suitable solvent, e.g., methylene chloride, after which the reaction is allowed to proceed at a suitable temperature, e.g., about 5° C. to about 35° C., for a suitable period of time, e.g., about 15 minutes to about 6 hours. The desired substituted 5-hydroxy-9,10-dioxo-9,10-dihydroanthracene-1-sulfonamide analogue, e.g., a compound of type 1.4, can be isolated by appropriate means including one or more of extraction, precipitation, filtration, recrystallization, and/or column chromatography, or other means as deemed appropriate and commonly known by the skilled artisan. The identity of the target compound can be determined using one or more of LC/MS-MS, 13C NMR, and/or 1H NMR, or other means as deemed appropriate and commonly known by the skilled artisan. As can be appreciated by one skilled in the art, alternative conditions can be used for the foregoing reactions. Further methods for the preparation of substituted 5-hydroxy-9,10-dioxo-9,10-dihydroanthracene-1-sulfonamide analogue, e.g., a compound of type 1.4, are disclosed in U.S. Pat. No. 9,783,513, which is incorporated herein by reference in its entirety.

b. Synthesis Route 2

In one aspect, the disclosed compounds of the present disclosure can be prepared generically by the synthesis scheme as shown below. All positions are defined herein.

Scheme 2A

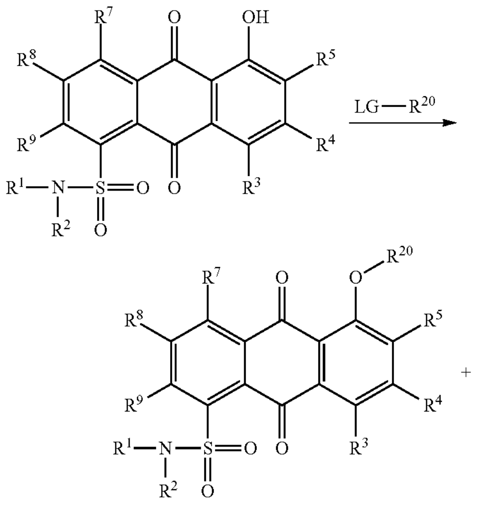

-continued

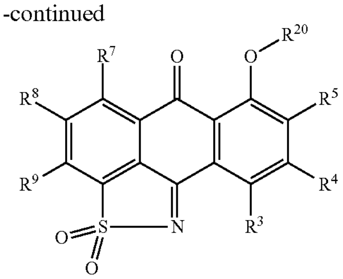

*LG: leaving group

Compounds are represented in generic form, with substituents as noted in compound descriptions elsewhere herein. A more specific example is set forth below.

Scheme 2B

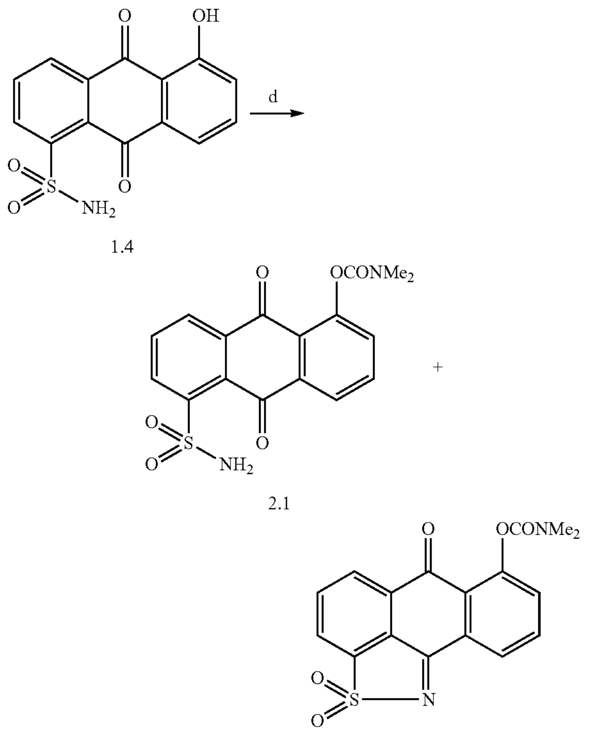

1.4

2.1

2.2 d: pyridine (64 eq), room temperature, $ClCONMe_2$.

The preparation of the disclosed compounds utilizes suitable substituted 5-hydroxy-9,10-dioxo-9,10-dihydroanthracene-1-sulfonamide analogue, e.g., a compound of type 1.4, prepared as described herein. Briefly, the suitable substituted 5-hydroxy-9,10-dioxo-9,10-dihydroanthracene-1-sulfonamide analogue, e.g., a compound of type 1.4, is suspended in a suitable solvent, e.g., pyridine, at a suitable temperature, e.g., about 5° C. to about 35° C., to which is added a suitable compound, such as LG-$R^{20}$, wherein LG is a suitable leaving group. In the specific case illustrated above, LG-$R^{20}$ is dimethylcarbamyl chloride. After addition of the LG-$R^{20}$ compound, the reaction is allowed to continue at a suitable temperature. e.g., about 5° C. to about 35° C., for a suitable period of time, e.g., about 15 minutes to about 30 hours. The desired disclosed target compound, e.g., a compound of type 2.1 and/or 2.2, can be isolated by appropriate means including one or more of extraction, precipitation, filtration, recrystallization, and/or column chromatography, or other means as deemed appropriate and commonly known by the skilled artisan. The identity of the target compound can be determined using one or more of LC/MS-MS, $^{13}C$ NMR, and/or $^{1}H$ NMR, or other means as deemed appropriate and commonly known by the skilled artisan. As can be appreciated by one skilled in the art, alternative conditions can be used for the foregoing reactions.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

Pharmaceutical Compositions

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally °Ccurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with an basoc reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985): Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson. Eds.): Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-s-cyclodextrin or sulfobutyl-s-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof: the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require of inhibition of STAT activity, e.g., STAT3 activity, an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for modulating STAT activity (e.g., treatment of one or more diseases or disorders such as an inflammatory disease, an autoimmune disease, including, but not limited to, multiple sclerosis, a cancer, or disease associated with a STAT3 dysfunction) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and a STAT, e.g., STAT3, inhibitor. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

Methods of Using the Compounds

In a further aspect, the present disclosure provides methods of treatment comprising administration of a therapeutically effective amount of a disclosed compound or pharmaceutical composition as disclosed herein above to a subject in need thereof. In various aspects, the method is for treatment of an inflammatory disease, an autoimmune disease, including, but not limited to, multiple sclerosis, a cancer, or disease associated with a STAT3 dysfunction, comprising administration of a therapeutically effective amount of a disclosed compound or pharmaceutical composition as disclosed herein above to a subject in need thereof.

In various aspects, disclosed herein are methods for the treatment of an inflammatory disorder in a mammal comprising the step of administering to the mammal a therapeutically effective amount of at least one disclosed compound, or a pharmaceutically acceptable salt thereof, or administering to the mammal a therapeutically effective amount of a disclosed pharmaceutical composition. In a further aspect, the mammal is a human. In a still further aspect, the mammal has been diagnosed with a need for treatment of the disorder prior to the administering step. In a yet further aspect, the method further comprises the step of identifying a mammal in need of treatment of the disorder.

In various aspects, the method is a method for treating an inflammatory disorder associated with STAT dysfunction. In a further aspect, the STAT is STAT3. In a still further aspect, the inflammatory disorder is an autoimmune disease. In a yet further aspect, the autoimmune disease is selected from autism, multiple sclerosis, rheumatoid arthritis, psoriasis, Crohn's disease, bacterially induced colitis, asthma, inflammatory bowel disease, scleroderma, type I diabetes, autoimmune pneumonitis, systemic lupus erythematosus, Sjogren's syndrome, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, asthma, vasculitis, cirrhosis, pemphigus vulgaris, autoimmune infertility, Goodpasture's disease, bullous pemphigoid, discoid lupus, ulcerative colitis, and dense deposit disease. In some aspects, the autoimmune disease is multiple sclerosis. In a further aspect, the inflammatory disorder is an allergic response, a neurodegenerative disease, or a fibrotic disease. In a still further aspect, the inflammatory disorder is selected from osteoarthritis, restenosis, artherosclerosis, and In various aspects, disclosed herein are methods for the treatment of a disorder of uncontrolled cellular proliferation in a mammal comprising the step of administering to the mammal administering a therapeutically effective amount of at least one disclosed compound, or a pharmaceutically acceptable salt thereof, or administering to the mammal a therapeutically effective amount of a disclosed pharmaceutical composition. In a further aspect, the mammal is a human. In a still further aspect, the mammal has been diagnosed with a need for treatment of the disorder prior to the administering step. In various aspects, the method further comprises the step of identifying a mammal in need of treatment of the disorder.

In various aspects, method is a method for treating a disorder of uncontrolled cellular proliferation associated with STAT dysfunction. In a still further aspect, the STAT dysfunction is associated with a STAT3 dysfunction. In a yet further aspect, disorder of uncontrolled cellular proliferation is a cancer. In an even further aspect, the disorder of uncontrolled cellular proliferation is selected from breast cancer, renal cancer, gastric cancer, colorectal cancer, multiple myeloma, leukemia; lymphomas, cutaneous T-cell lymphoma, Hodgkin's disease; and solid tumors.

In various aspects, disclosed herein are methods for inhibiting STAT activity in a mammal comprising the step of administering to the mammal administering a therapeutically effective amount of at least one disclosed compound, or a pharmaceutically acceptable salt thereof, or administering to the mammal a therapeutically effective amount of a disclosed pharmaceutical composition. In a further aspect, the mammal is a human. In a still further aspect, the mammal has been diagnosed with a need for inhibiting STAT activity prior to the administering step. In some aspects, the method for inhibiting STAT activity in a mammal comprising the step of administering to the mammal administering a therapeutically effective amount of at least one disclosed compound, or a pharmaceutically acceptable salt thereof, or administering to the mammal a therapeutically effective amount of a disclosed pharmaceutical composition further comprises the step of identifying a mammal in need for inhibiting STAT activity. In some aspects, the method further comprises the step of identifying a mammal in need for inhibiting STAT3 activity.

In various aspects, disclosed herein are methods for inhibiting STAT activity in at least one cell, comprising the step of contacting the at least one cell with an effective amount of at least one disclosed compound, or a pharmaceutically acceptable salt thereof, or administering to the mammal a therapeutically effective amount of a disclosed pharmaceutical composition. In a further aspect, the cell is mammalian. In a still further aspect, the cell is human.

In some aspects, disclosed are methods for inhibiting STAT activity in at least one cell, comprising the step of contacting the at least one cell with an effective amount of at least one disclosed compound, or a pharmaceutically acceptable salt thereof, or administering to the mammal a therapeutically effective amount of a disclosed pharmaceutical composition. In a further aspect, the cell is mammalian, wherein the cell has been isolated from a mammal prior to the contacting step.

In other aspects, disclosed are methods for inhibiting STAT activity in at least one cell, comprising the step of contacting the at least one cell with an effective amount of at least one disclosed compound, or a pharmaceutically acceptable salt thereof, or administering to the mammal a therapeutically effective amount of a disclosed pharmaceutical composition. In a further aspect, the cell is mammalian, wherein contacting the cell is via administration to a mammal.

In various aspects, disclosed are methods for inhibiting STAT activity in at least one cell, comprising the step of contacting the at least one cell with an effective amount of at least one disclosed compound, or a pharmaceutically acceptable salt thereof, or administering to the mammal a therapeutically effective amount of a disclosed pharmaceutical composition. In a further aspect, the cell is mammalian, wherein the mammal has been diagnosed with a need for inhibiting STAT activity prior to the administering step.

In various aspects, disclosed are methods for inhibiting STAT activity in at least one cell, comprising the step of contacting the at least one cell with an effective amount of at least one disclosed compound, or a pharmaceutically acceptable salt thereof, or administering to the mammal a therapeutically effective amount of a disclosed pharmaceutical composition, wherein the method further comprises a step of diagnosing the mammal a need for treatment of a disorder related to STAT activity prior to the administering step.

In various aspects, In other aspects, disclosed are methods for inhibiting STAT activity in at least one cell, comprising the step of contacting the at least one cell with an effective amount of at least one disclosed compound, or a pharmaceutically acceptable salt thereof, or administering to the mammal a therapeutically effective amount of a disclosed pharmaceutical composition, wherein the STAT activity inhibited is STAT3 activity.

Kits

In various aspects, disclosed herein are kits comprising at least one disclosed compound, or a pharmaceutically acceptable salt thereof, or a disclosed pharmaceutical composition; and one or more of the following: at least one agent known to increase STAT activity; at least one agent known to decrease STAT activity; at least one agent known to treat a inflammatory disorder; at least one agent known to treat a disease of uncontrolled cellular proliferation; instructions for treating a disorder associated with a STAT dysfunction; instructions for treating an inflammatory disorder, or instructions for treating a disease of uncontrolled cellular proliferation.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

Research Tools

The disclosed compounds and pharmaceutical compositions have activity as inhibitors of STAT activity, e.g., STAT3 activity. As such, the disclosed compounds are also useful as research tools. Accordingly, one aspect of the present disclosure relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a STAT, e.g., STAT3, assay that can be conducted in vitro or in a cell culture system. Still another aspect of the invention relates to a method of studying a biological system, e.g., a model animal for a clinical condition, or biological sample comprising a STAT protein, e.g., a STAT3 protein, the method comprising: (a) contacting the biological system or sample with a compound of the invention; and (b) determining the effects caused by the compound on the biological system or sample.

In some aspects, the disclosed compounds can be useful as a control compound when screening other compounds for efficacy in an animal model of an inflammatory disease, an autoimmune disease, including, but not limited to, multiple sclerosis, a cancer, or other disease associated with a STAT3 dysfunction.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Animals. B6/WT, B10PL/WT and SJL/WT mice were purchased from the Jackson Laboratory and bred in a specific pathogen-free animal facility at Ohio State University (OSU) Wexner Medical Center. B10.PL mice transgenic for the MBP Ac1-11-specific TCR chains Vα2.3 or Vs8.2 (Goverman, Woods et al. 1993) were also bred in a specific pathogen-free animal facility at Ohio State University (OSU) Wexner Medical Center. All animal protocols were approved by the OSU Institutional Animal Care and Use Committee.

In vitro culture of splenocytes from TCR transgenic mice. Splenocytes were prepared from naïve 5-10-wk-old Vα2.3/Vβ8.2 TCR transgenic mice and cultured in 24-well plates at $2\times10^8$ cells/well with irradiated B10.PL splenocytes ($6\times10^8$ cells/well). Cells were activated with of MBP Ac1-11 (10 μg/ml) and different combination of cytokines or neutralizing antibodies for cytokines to differentiate effector T helper cells. Cytokines and antibody concentrations were as follows: 0.5 ng/ml IL-12, 25 ng/ml IL-6, 1 ng/ml TGFβ1, 2 μg/ml anti-IFNγ, 1 μg/ml anti-IL-12, 2 μg/ml anti-IL-4, and 0.35 μg/ml anti-TGFβ (Yang, Weiner et al. 2009).

EAE Induction. Immunization: 8-10 week old B6/WT or SJL/WT mice were s.c. injected over four sites in the flank with 200 μg MOG 35-55 or PLP 135-151 (CS bio) in an emulsion with CFA (Difco). 200 ng pertussis toxin (List) per mouse in PBS was injected i.p. at the time of immunization and 48 h later. Adoptive transfer: Splenocytes were isolated from naïve 5-10-week-old Vα2.3/Vβ8.2 TCR transgenic mice and activated with 10 μg/ml of MBP Ac1-11 with or without rmIL-6 in 24-well plates at $2\times10^8$ cells/well with irradiated B10.PL splenocytes ($6\times10^8$ cells/well). After 72 hours, the cells were washed with PBS and $8\times10^6$ were injected i.p. into naïve B10.PL mice. Evaluation. The mice were evaluated daily for clinical signs of EAE. Mice were scored on scale of 0 to 6:0, no clinical disease; 1, limp/flaccid tail; 2, moderate hind limb weakness; 3. severe hind limb weakness; 4. complete hind limb paralysis; 5 quadriplegia or premoribund state; and 6, death.

ELISA Assay. ELISA was performed to detect the expression of IL-17 and IFNγ in supernatant. Purified anti-mouse IL-17 primary antibody (BD bioscience) was diluted in 0.1 M $NaHCO_3$ (pH 8.2) at 2 μg/ml while purified anti-mouse IFNγ primary antibody was diluted in 0.1M $NaHCO_3$ (pH 9.5) at 2 μg/ml. Immunolon II plates (Dynatech Laboratories) were coated with 50 μl of primary antibodies per well and incubated overnight at 4° C. The plates were washed twice with PBS/0.05% Tween 20. The plates were blocked with 200 μl of 1% BSA in PBS per well for 2 h. The plates were washed twice with PBS/0.05% Tween 20, and 100 μl of supernatants were added in duplicate. The plates were incubated over-night at 4° C. and washed four times with PBS/0.05% Tween 20. Biotinylated rat anti-mouse secondary antibody (BD bioscience) were diluted in PBS/1% BSA, 100 μl of 1 μg/ml biotinylated antibody was added to each well, and plates were incubated at room temperature for 1 h. The plates were washed six times with PBS/0.05% Tween 20, and 100 μl avidin-peroxidase was added at 2.5 μg/ml and incubated for 30 min. The plates were washed eight times with PBS/0.05% Tween 20, and 100 μl ABTS substrate containing 0.03% $H_2O_2$ (for IL-17) or TMB substrate (for IFNγ) was added to each well. The plate was monitored for 10-20 min for color development and read at A 405. A standard curve was generated from cytokine standard, and the cytokine concentration in the samples was calculated.

Intracellular staining and flow cytometric analysis. Flow cytometric analysis was performed to evaluate the expression of surface markers and T-bet in CD4 T cells, as previously described (Yang, Weiner et al. 2009). Briefly, splenocytes were activated with antigen or αCD3/CD28 for 48 to 72 hours. Cells were then collected, washed, and resuspended in staining buffer (1% BSA in PBS). The cells were incubated with mAbs to the cell-surface markers for 30 min at 4° C. After washing twice with staining buffer, cells were fixed and permeabilized using Cytofix/Cytoperm solution for 20 min at 4° C. Cells were stained for intracellular cytokines and T-bet for 30 min at 4° C. 80,000-100,000 live cell events were acquired on a FACSCanto (BD) and analyzed using FlowJo software (Tree Star, Inc.). PerCP-anti-CD4, and Pacific Blue-anti-CD44 were purchased from BD. PE-anti-PD-1, PE-Cy7-anti-IL-7Rα and Pacific Blue-anti-T-bet were purchased from Biolegend Biotechnology, Inc.

CFSE-based proliferation assays. Splenocytes were suspended at 1×106/ml in PBS and incubated with CFSE (1-5 μM) at 37° C. for 20 min. Then 5 volume of EAE medium was added to the cell suspension followed by one additional wash with PBS (2% FBS). Cells were then suspended in EAE medium and cultured at 4×106/ml in 24-well plates with MBP Ac1-11 (10 μg/mL) in the presence of LLL12 or DMSO for 2-7 days, followed by flow cytometric analysis of cell surface markers and CFSE.

Statistical analysis. GraphPad software (GraphPad Prism Software, Inc., San Diego, Calif., USA) was utilized for statistical analysis. A statistically significant difference in EAE clinical scores was considered to be P<0.05, as determined by Mann-Whitney U-test. The Mann-Whitney U-test is non-parametric, and therefore accounts for the fact that EAE scores are ordinal and not interval-scaled. ELISA and quantitated flow data comparisons were performed using two-tailed unpaired Student's t-tests. Differences with P<0.05 were considered significant.

Synthesis of LLL-12. The overall synthesis of LLL-12 and LLL-12b is as shown in the synthetic scheme below.

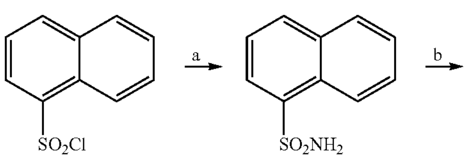

1 2

-continued

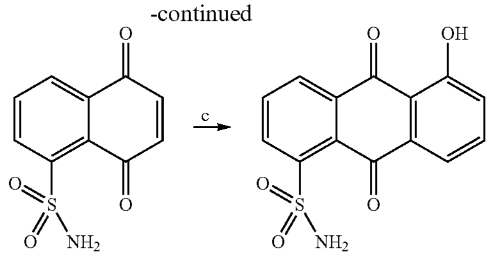

3 LLL-12 a: actone, $NH_3$•$H_2O$, room temperature/3 h;
b: $Cr_2O_3$, $HOAc/H_2O$, <80° C.;
c: $CH_2Cl_2$/MeOH, $Et_3N$ (0.02 eq), 3-hydroxy-2H-pyran-2-one, -20-10° C., then room temperature/2-3 h.

1-naphthalenesulfonyl chloride (1, 50 g) was stirred with 28% ammonium hydroxide (300 mL) in acetone (1 L) at room temperature for about 3 h, then the reaction mixture was concentrated by rotary evaporation at about 60° C. (water bath) to 500-600 mL, cooled to room temperature, and 1.5 L of water was added slowly while stirring. Then the formed white precipitate was filtered and washed with 2 L of water. After dried by air, 42 g of white powder 1-naphthalenesulfonamide (2) was obtained in the yield of 91.8%.

The compound 2 (24 g) was suspended in acetic acid (300 mL) and was heated to dissolved completely, then cooled to 40~45° C. (water bath), and $CrO_3$ (52 g) solution in $H_2O$ (50 mL) and acetic acid (50 mL) was added over 1~1.5 h and the water bath temperature was maintained around 42° C. After the addition, the reaction mixture was stirred for additional 2 h at room temperature. Then 1 L of water was added and filtered. The obtained yellow solid was washed with large amount of water and dried by air. $^1H$ NMR spectrum of the crude product indicated that it contained about 50% of starting material 2 besides the desired 5,8-dioxo-5,8-dihydronaphthalene-1-sulfonamide (3).

The crude product (36 gm from 6 batch reactions) was dissolved in minimum acetone at room temperature and hexane was added till precipitate was just observed, then place it in refrigerator (about −20° C.) overnight. Filtration afforded 13.6 g of compound 3 with purity of 93%, the final yield was about 8.3%.

The compound 3 (5.73 g, 24 mmol) was dissolved in $CH_2Cl_2$ (350-400 mL) and methanol (55~60 mL) at room temperature, then cooled to −20~−15° C. and $Et_3N$ (0.57 mL) was added. After stirring for about 15 min. 3-hydroxy-1-pyrone (3.24 g, 25.5 mmol) in 100 mL of $CH_2Cl_2$ was added and stirred for about 30 min, then 2-3 h at room temperature. H2O (about 300 mL) was added, stirred for a while, and filtered to collect precipitate. The yellow-greenish solid washed with H2O, then $CH_2Cl_2$, vacuumed to dryness. Although the $^1H$ NMR spectrum (in DMSO-d6) indicated the product (2.3 g, yield~30%) is pure (>95%), the further purification was done by recrystallization from acetone and column chromatography. The product was dissolved in minimum acetone at boiling point and then cooled to room temperature, placed it in refrigerator (about ~20° C.) overnight. Filtration afforded 1.1 g of yellow powder compound LLL-12 with purity of ~99% (based on NMR). The filtrate was added 2 volumes of hexane and applied to silica gel column and eluted with mixed solvent of acetone and hexane (1:1, VV). The fraction containing LLL-12 was collected and the solvent was evaporated to afford $2^{nd}$ crop of LLL-12 (about 0.4 g), the final total yield was 1.5 g (20.6%).

Synthesis of LLL-12b and Compound 4. The preparation of LLL12b and compound 4 from LLL12 was either by Method A or Method B as described herein below.

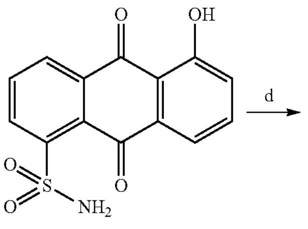

LLL12

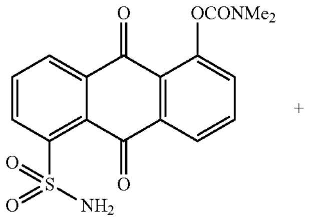

LLL12b

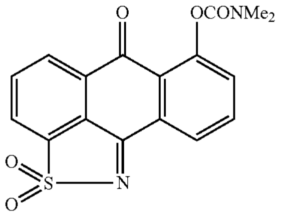

4 d: pyridine (64 eq), room temperature, $ClCONMe_2$.

Method A: LLL-12 (192 mg, 0.635 mmol) was suspended in pyridine (3.2 g, 64 eq) at room temperature, then dimethylcarbamyl chloride (81 mg, 0.753 mmol) was added and stirred at room temperature overnight. Then the reaction mixtures were filtered and washed with $CH_2Cl_2$ to afford the compound of LLL12b (86 mg, yield 36%).

Method B: LLL-12 was dissolved completely in pyridine, e.g., for example, LLL12 (0.1 g, 0.33 mmol) was dissolved in pyridine (6 g, 75.9 mmol, 230 eq), then dimethylcarbamyl chloride (36 mg, 0.33 mmol) was added and stirred at room temperature overnight), the desired LLL-12-$CO_2NMe_2$ was not obtained. The workup is as follows: to the reaction solution, $H_2O$ was added and the precipitate was collected by filtration and dried by air; then the solid was subjected to column chromatography (silical gel) and eluted with $CH_2Cl_2$ and then EtOAc:Hexane (1:1). The main fraction was the compound 4, the intramolecular condensation reaction product.

Synthesis of LLL12-COBu-t and Compound 5. The preparation of LLL12-COBu-t compound 5 from LLL12 was either by Method A or Method B as described herein below.

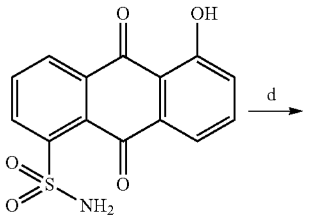

LLL12

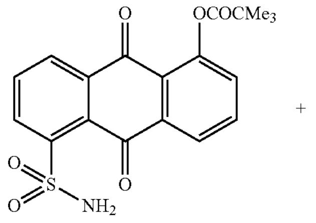

LLL12-COBu-t

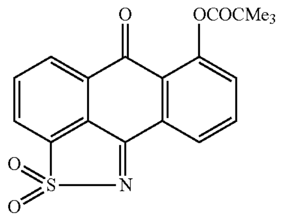

5 f: pyridine (64 eq), 0° C., $ClCOCMe_3$

Method A: LLL12 (38 mg, 0.125 mmol) was suspended in pyridine (0.63 g, 7.96 mmol, 64 eq) at room temperature, then trimethyl acetylchloride (18.1 mg, 0.150 mmol) was added and stirred for 3 days at room temperature. The small quantity of insoluble green material, which was confirmed to be starting material LLL12 by NMR, was removed by filtration. The filtrate was evaporated to remove solvent, the remains were washed with $H_2O$ and applied to column chromatography (Silica gel, EtOAc:Hexane=1:1). The main fractions were the compound 5, the intramolecular condensation reaction product.

Method B: The same reaction as Method A above was carried out overnight at 0° C. After the reaction, the reaction mixtures were filtered to remove insoluble yellow solid and the filtrate was added $H_2O$ to precipitate. The precipitate was collected by filtration, washed with $H_2O$, dried by air and applied to column chromatography (Silica gel. EtOAc: Hexane=1:1). The fraction containing the desired compound LLL12-COBu-t was collected, the further purification was done by twice column chromatography (Silica gel, EtOAc: Hexane=1:2) and 5.8 mg (11% yield) of LLL12-COBu-t was obtained.

Figure 3A:
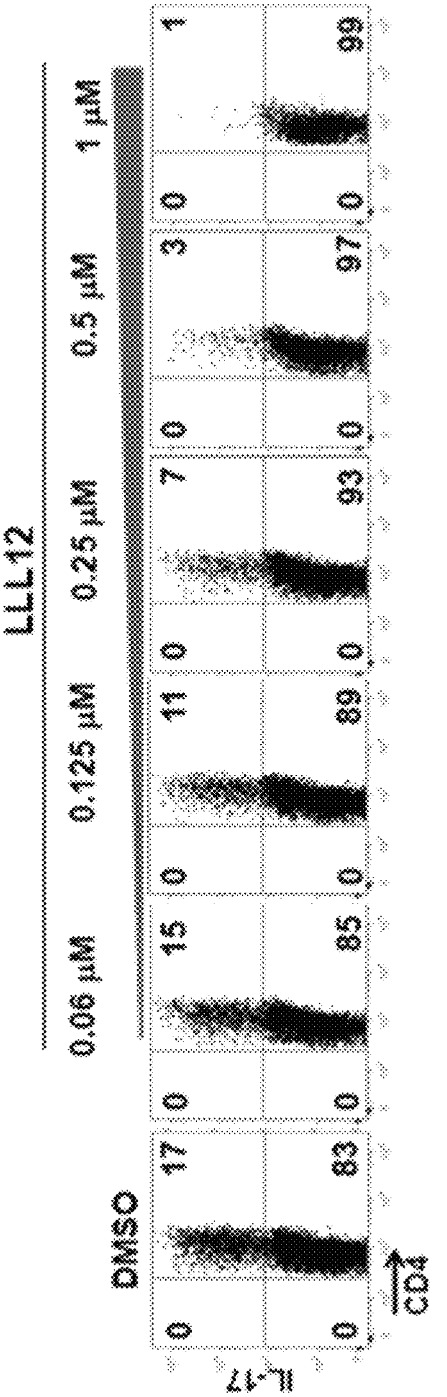
FIGS. 3A-3B show representative data for inhibition of IL-17 in myelin-specific CD4 T cells by LLL12. Briefly, splenocytes from naïve TCR αβ transgenic mice were activated with MBP Ac1-11 plus TGF-β and IL-6, with or without the indicated concentration of LLL12 for 3 days.
Figure 3B:
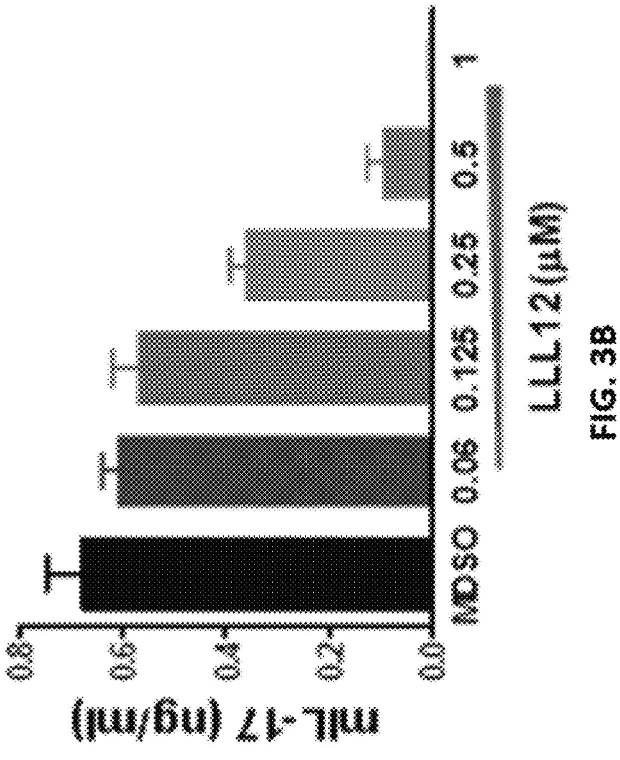
Figure 4:
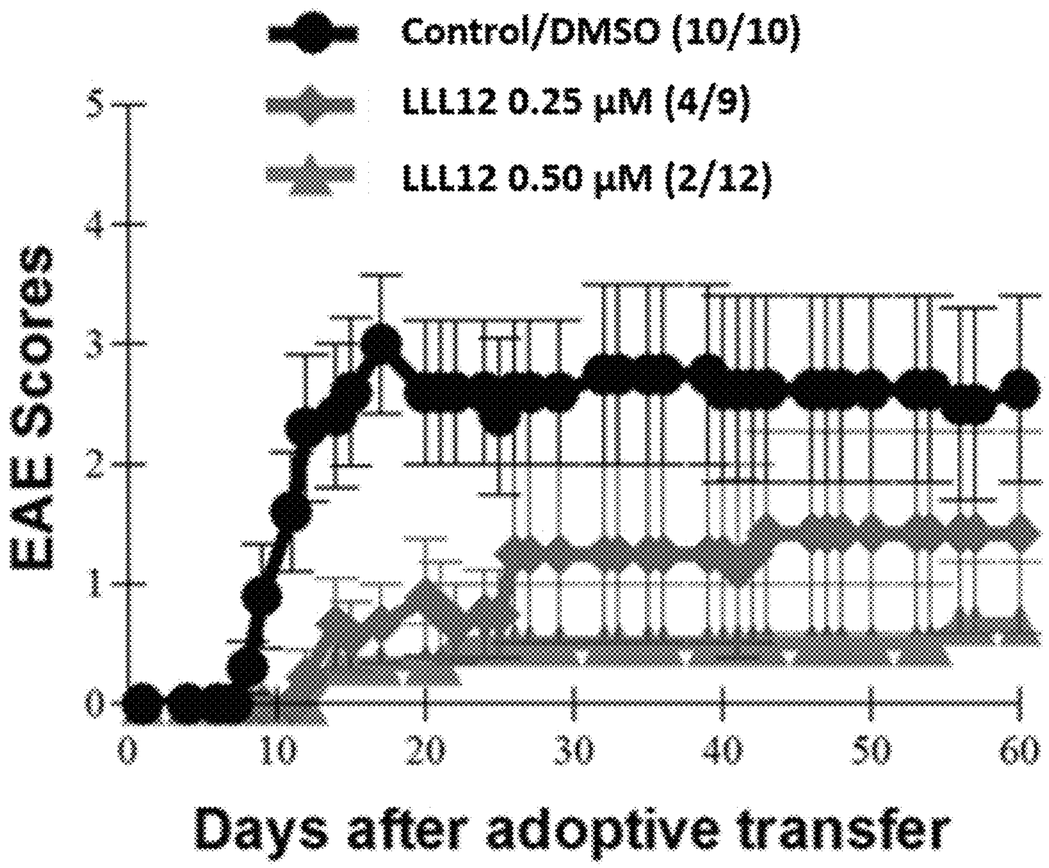
FIG. 4 shows representative data demonstrating that the LLL12 inhibits T cell encephalitogenicity in adoptive transfer. Briefly, splenocytes from naïve TCR transgenic mice were activated with MBP Ac1-11 plus IL-6 for 3 days, in the presence of LLL12 at 0.25 mM or 0.5 mM. DMSO was used as vehicle control. The cells were then adoptively transferred into naïve B10PL mice (disease incidence). Data are representative of multiple independent experiments. The treatment conditions with control (DMSO) or drug are as indicated in the figure.

LLL12 Is effective in an EAE model of MS. The data shown in FIGS. 3A, 3B and 4 show the efficacy of LLL12 in the treatment in an EAE model of MS. FIGS. 3A-3B show representative data for inhibition of IL-17 in myelin-specific CD4 T cells by LLL12. Briefly, splenocytes from naïve TCR αβ transgenic mice were activated with MBP Ac1-11 plus TGF-β and IL-6, with or without the indicated concentration of LLL12 for 3 days. FIG. 3A shows intracellular flow cytometric data obtained from cells gated on live CD4+ CD44+ cells that were either not exposed to LLL12 (DMSO control, first panel) or to increasing concentrations of LLL12 (second panel to fifth panel). FIG. 3B shows IL17 production data as determined by ELISA analysis of supernatants from the cells used in the analysis for FIG. 3A. FIG. 4 shows representative data demonstrating that the LLL12 inhibits T cell encephalitogenicity in adoptive transfer. Briefly, splenocytes from naïve TCR transgenic mice were activated with MBP Ac1-11 plus IL-6 for 3 days, in the presence of LLL12 at 0.25 mM or 0.5 mM. DMSO was used as vehicle control. The cells were then adoptively transferred into naïve B10PL mice (disease incidence). Data are representative of multiple independent experiments. The treatment conditions with control (DMSO) or drug are as indicated in the figure.

Figure 2:
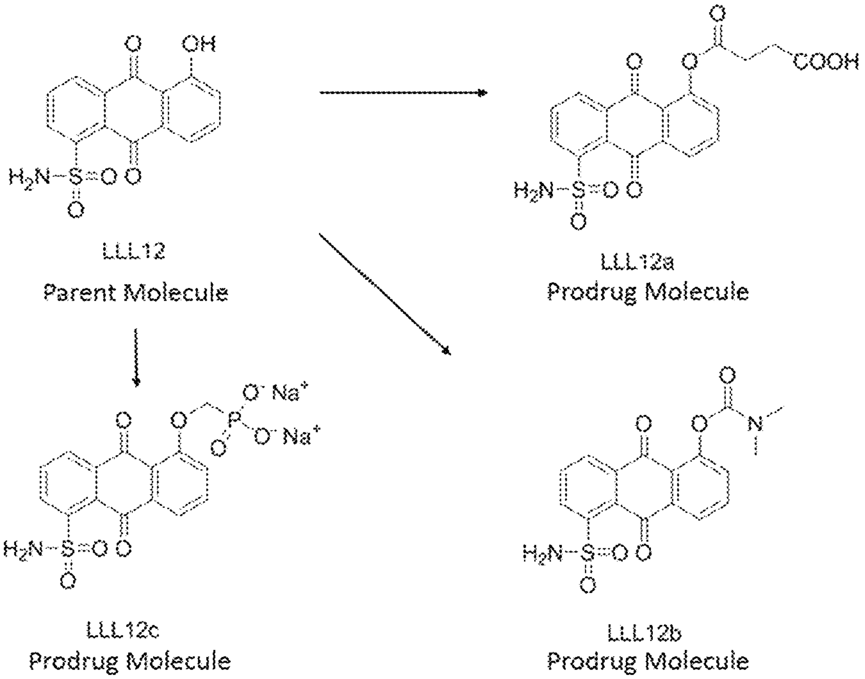
FIG. 2 shows the chemical structure of LLL12 and representative disclosed prodrugs based on the LLL12 structure. The designation used for the prodrugs are as given in the figure, LLL12a, LLL12b, and LLL12c.
Figure 5A:
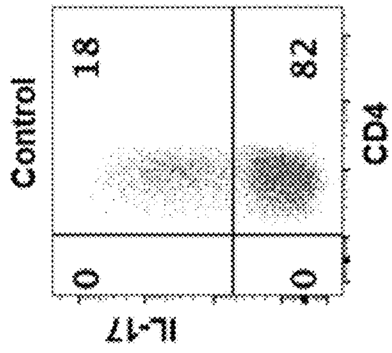
FIGS. 5A-5C show representative data for inhibition of IL-17 in myelin-specific CD4 T cells by LLL12 prodrugs. Briefly, splenocytes from naïve TCR αβ transgenic mice were activated with MBP Ac1-11 plus TGF-β and IL-6, with or without the indicated concentration of the indicated LLL!2 prodrug for 3 days.
Figure 5B:
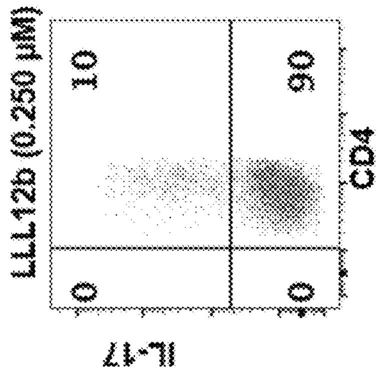
Figure 5C:
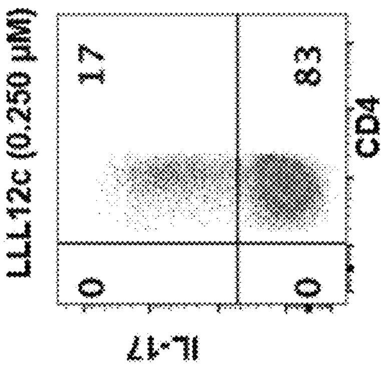
Figure 5D:
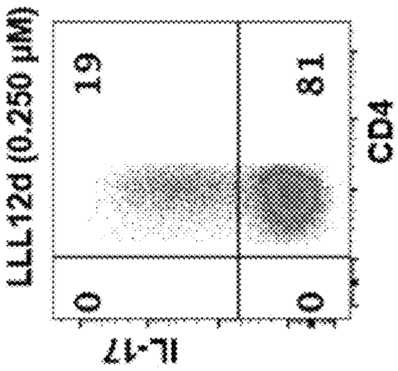
FIG. 5D shows intracellular flow cytometric data obtained from cells gated on live CD4+CD44+ cells that were exposed to 0.25 μM LLL12c.
Figure 5E:
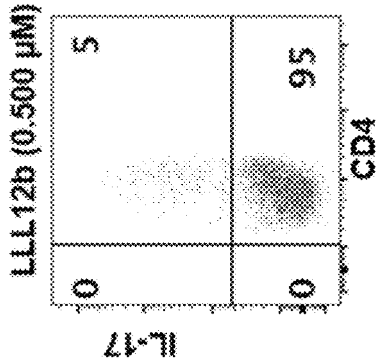
FIG. 5E shows intracellular flow cytometric data obtained from cells gated on live CD4+CD44+ cells that were exposed to 0.50 μM LLL12b.
Figure 5F:
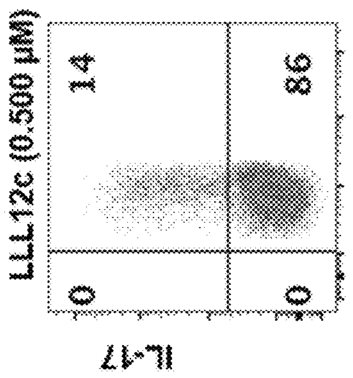
FIG. 5F shows intracellular flow cytometric data obtained from cells gated on live CD4+CD44+ cells that were exposed to 0.50 μM LLL12c.
Figure 5G:
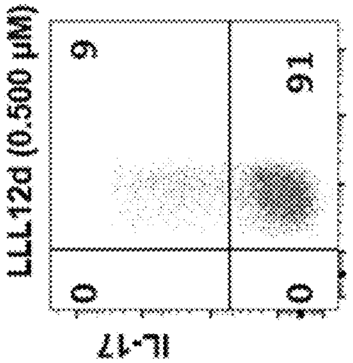
FIG. 5G shows intracellular flow cytometric data obtained from cells gated on live CD4+CD44+ cells that were exposed to 0.50 μM LLL12c.

STAT3 prodrugs based on LLL12 Inhibit IL-17 production in myelin-specific CD4 T cells. Three STAT3 prodrugs, LLL12b, LLL12c and LLL12d (see FIG. 2 for structures), were designed and synthesized. FIGS. 5A-5C show representative data for inhibition of IL-17 in myelin-specific CD4 T cells by LLL12 prodrugs. Briefly, splenocytes from naïve TCR αβ transgenic mice were activated with MBP Ac1-11 plus TGF-β and IL-6, with or without the indicated concentration of the indicated LLL!2 prodrug for 3 days. FIG. 5A shows intracellular flow cytometric data obtained from cells gated on live CD4+CD44+ cells that were not exposed to drug (DMSO-treated control cells). FIG. 5B shows intracellular flow cytometric data obtained from cells gated on live CD4+CD44+ cells that were exposed to 0.25 μM LLL12b. FIG. 5C shows intracellular flow cytometric data obtained from cells gated on live CD4+CD44+ cells that were exposed to 0.25 μM LLL12c. FIG. 5D shows intracellular flow cytometric data obtained from cells gated on live CD4+CD44+ cells that were exposed to 0.25 μM LLL12c. FIG. 5E shows intracellular flow cytometric data obtained from cells gated on live CD4+CD44+ cells that were exposed to 0.50 μM LLL12b. FIG. 5F shows intracellular flow cytometric data obtained from cells gated on live CD4+CD44+ cells that were exposed to 0.50 μM LLL12c. FIG. 5G shows intracellular flow cytometric data obtained from cells gated on live CD4+CD44+ cells that were exposed to 0.50 μM LLL12c The data show that when these compounds were cultured with myelin-specific CD4 T cells in vitro, LLL12b and LLL12d significantly suppress IL-17 production in myelin-specific CD4 T cells, while LLL12c a much decreased effect in suppressing IL-17 production (FIGS. 5A-5G). 0.25 μM of LLL12b suppresses 44% of IL-17 production while 0.50 μM of LLL12b suppresses 72% of IL-17 production in murine myelin-specific CD4 T cells. For LLL12d, 50% of IL-17 production was suppressed by 0.50 μM of LLL12d although no suppression was observed at 0.25 μM level.

Figure 6A:
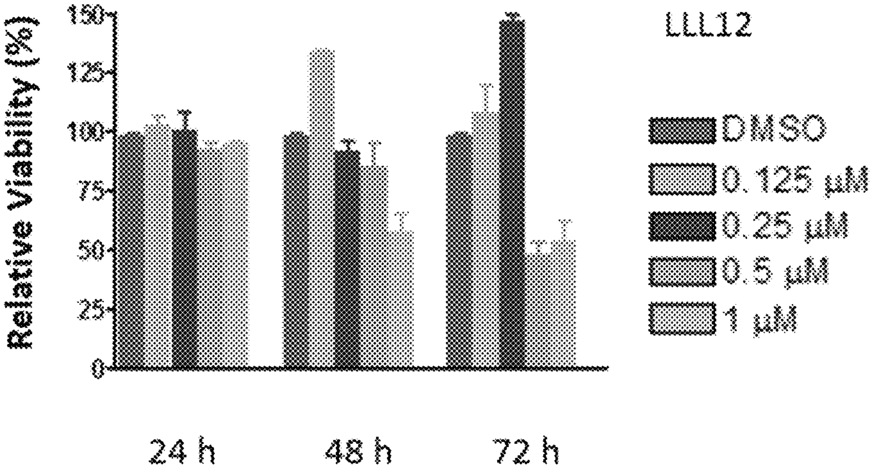
FIGS. 6A-6C show representative data for cell viability after treatment with DMSO or the indicated concentration of the indicated representative prodrug at 24 h, 48 h, and 72 h post-treatment. The data were obtained using a trypan blue exclusion assay using splenocytes from naïve TCR transgenic mice that were cultured as described.
Figure 6B:
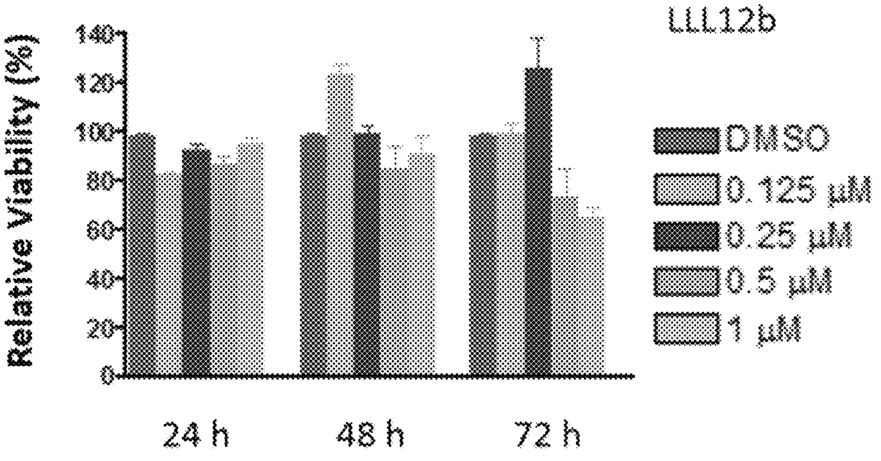
Figure 6C:
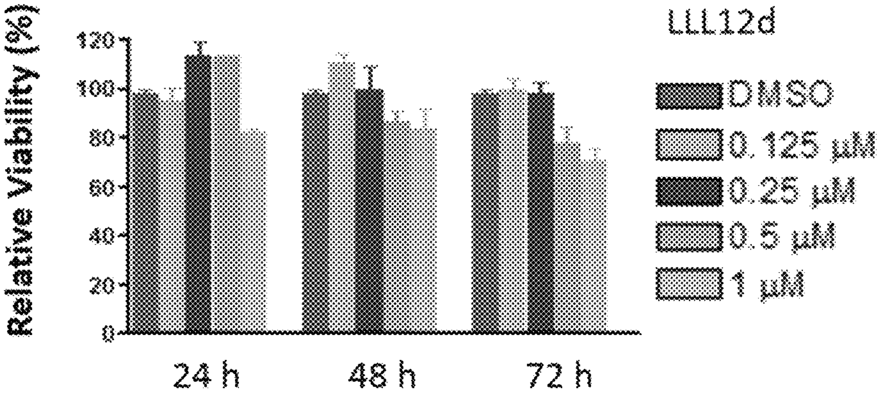

In vitro toxicity evaluation of new STAT3 prodrugs. Cellular toxicity testing was carried out using a trypan blue exclusion assay as described herein. FIGS. 6A-6C show representative data for cell viability after treatment with DMSO or the indicated concentration of the indicated representative prodrug at 24 h, 48 h, and 72 h post-treatment. The data were obtained using a trypan blue exclusion assay using splenocytes from naïve TCR transgenic mice that were cultured as described. These data show that prodrugs LLL12b and LLL12d have minimal cellular toxicity at the doses showing significant suppression of IL-7 production in myelin-specific CD4 T cells (FIGS. 6A-6C).

Figure 7A:
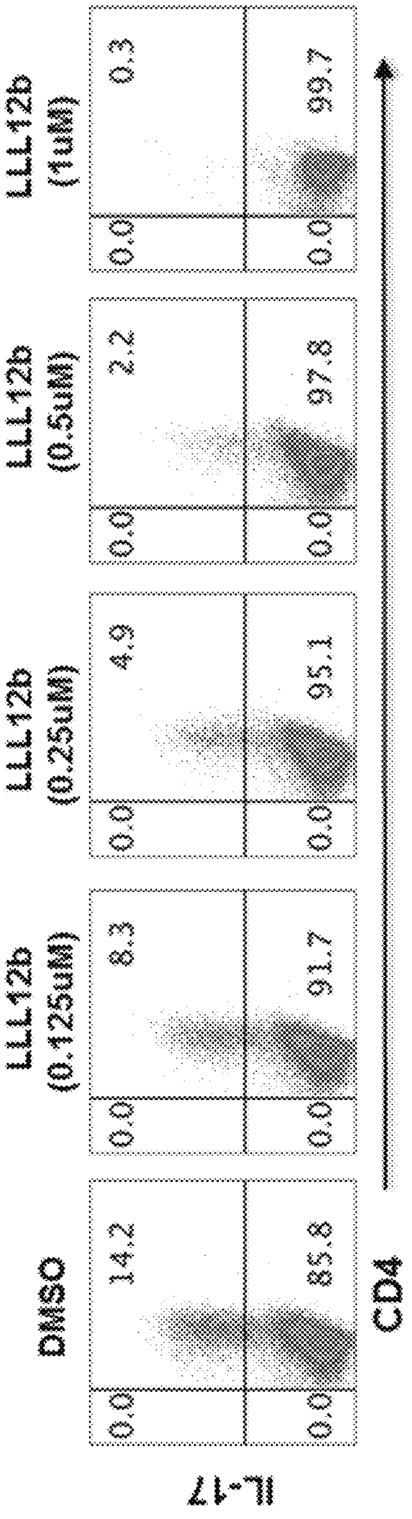
FIGS. 7A-7B show representative data for the effect of a representative disclosed compound, LLL12b, on IL-17 production, pSTAT3 levels, and cell viability under various conditions.
Figure 7B:
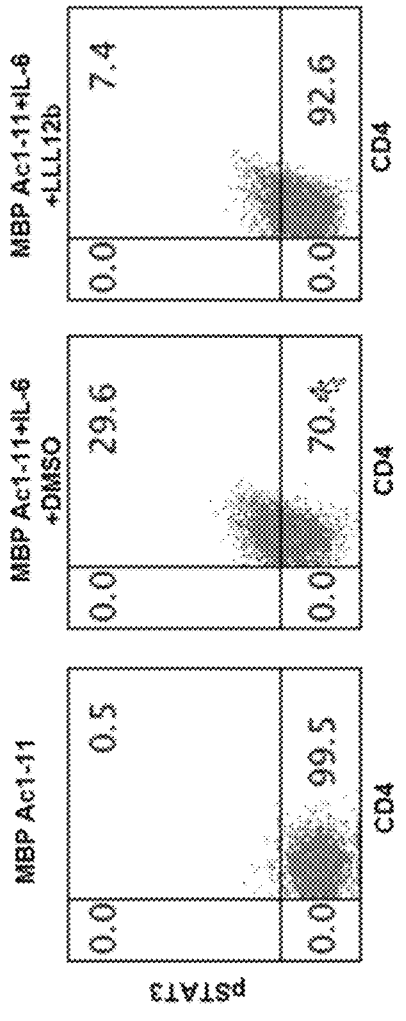

LLL12b suppresses pSTAT3 expression and IL-17 production in myelin-specific CD4 T cells in a dose-dependent manner. LLL21b was further tested to assess suppression of pSTAT3 expression in myelin-specific CD4 T cells. FIGS. 7A-7B show representative data for the effect of a representative disclosed compound, LLL12b, on IL-17 production, pSTAT3 levels, and cell viability under various conditions. FIG. 7A shows representative data on the IL-17 production in myelin-specific CD4 T cells that were not treated with a disclosed compound (DMSO control treatment) compared to the indicated concentrations of treatment with LLL12b. The data were obtained by intracellular flow cytometric analysis. The data show a dose-dependent inhibition of IL-17 production in these cells. FIG. 7B shows representative data on the pSTAT3 levels in myelin-specific CD4 T cells under the indicated conditions (MBP Ac1-1 activation, MBP Ac1-1 and IL-6 activation with DMSO control treatment, and MBP Ac1-1 and IL-6 activation with 0.025 μM LLL12b treatment). The data were obtained by intracellular flow cytometric analysis. The data show LLL12b-dependent inhibition of pSTAT3 levels in these cells. As shown in FIG. 7A, the data show that prodrug LLL12b inhibits myelin-specific IL-17 production in a dose-dependent manner. Furthermore, the data (FIG. 7B) show that 0.250 μM of LLL12b notably suppresses pSTAT3 expression.

Figure 8A:
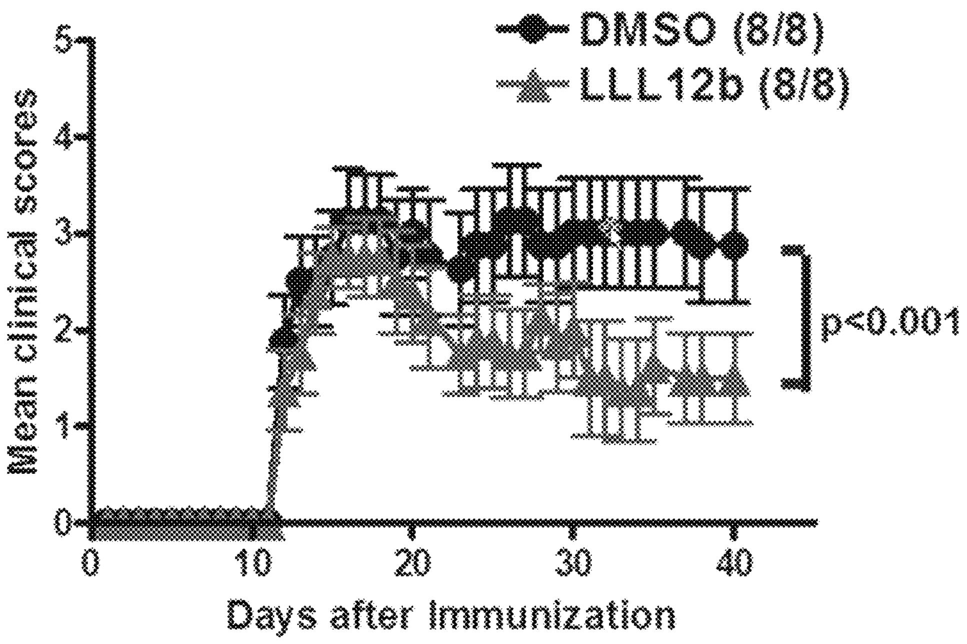
FIGS. 8A-8B show representative data for the effect of a representative disclosed compound, LLL12b, for suppression of EAE development in a chronic EAE model of MS. Briefly, naïve WT/B6 mice were immunized with MOG 35-5. LLL12b (10 mg/kg in DMSO) or DMSO was injected into immunized B6 mice at 10 mg/kg for 7 days from day 14 to day 20 when 80% of the mice showed clinical signs of EAE.
Figure 8B:
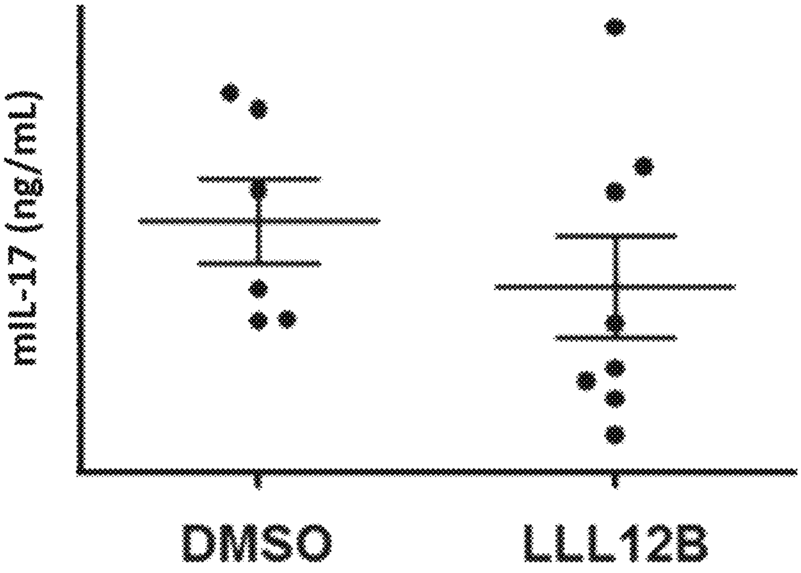

LLL12b significantly suppresses EAE development in chronic EAE model of MS In vivo. The in vivo efficacy of LLL12b was also evaluated in chronic EAE model of MS in immunized B6 mice by treating EAE mice with 10 mg/ml of LLL12b for 7 days after disease onset. FIGS. 8A-8B show representative data for the effect of a representative disclosed compound, LLL12b, for suppression of EAE development in a chronic EAE model of MS. Briefly, naïve WT/B6 mice were immunized with MOG 35-5. LLL12b (10 mg/kg in DMSO) or DMSO was injected into immunized B6 mice at 10 mg/kg for 7 days from day 14 to day 20 when 80% of the mice showed clinical signs of EAE. FIG. 8A shows presentative mean clinical score data from a representative experiment out three independent experiments. The data show a statistically significant suppression in the mean clinical score reflecting the suppression of EAE development in animals treated with LLL12b. FIG. 8B shows data for IL-17 production determined using ELISA for samples from splenocytes isolated from mice that had been treated with DMSO or LLL12b, and then activated with MOG 35-5 for 3 days. The data show decreased production of IL-17 in animals that had been treated with LLL12b. The data show that therapeutic administration of LLL12b significantly suppresses EAE development in treated mice (FIG. 8A). The data (FIG. 8B) also show that LLL12b treated mice have decreased IL-17 production.

Figure 9A:
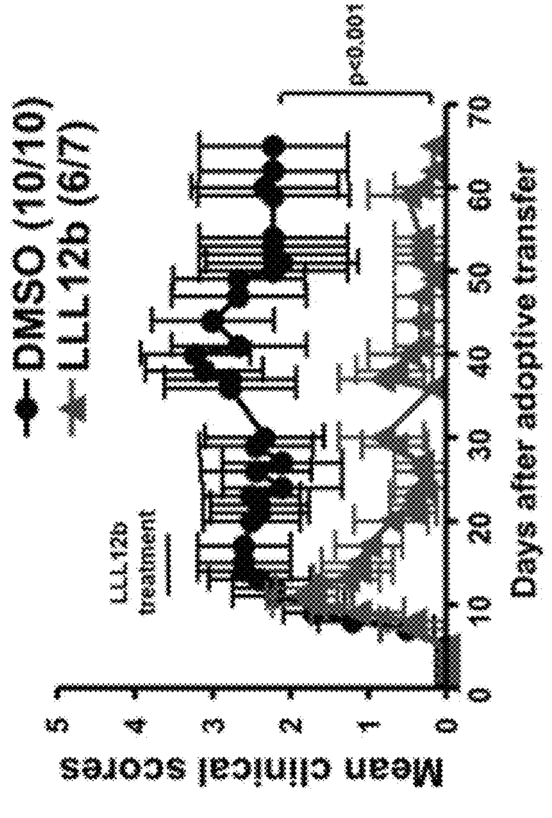
FIGS. 9A-9C show representative data for the effect of a representative disclosed compound, LLL12b, on suppression of EAE development in an adoptive transfer EAE model of MS.
Figure 9B:
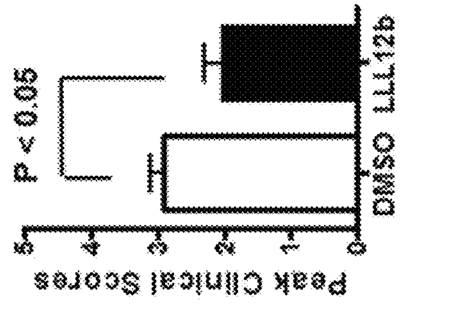
Figure 9C:
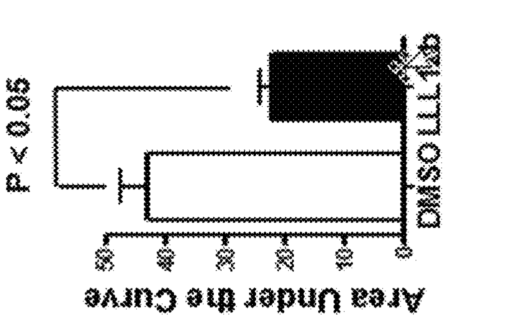

Novel prodrug LLL12b significantly suppresses EAE development in adoptively transferred EAE In vivo. The in vivo efficacy of LLL12b was evaluated in adoptively transferred EAE model by treating EAE mice with 10 mg/ml of LLL12b for 7 days after disease onset. FIGS. 9A-9C show representative data for the effect of a representative disclosed compound, LLL12b, on suppression of EAE development in an adoptive transfer EAE model of MS. FIG. 9A shows presentative mean clinical score data from a representative experiment out of four independent experiments in which splenocytes from naïve TCR transgenic mice were activated with MBP Ac1-11 plus IL-6 for 3 days, and then injected into naïve B10PL mice. The mice were then treated with either DMSO or a representative disclosed compound, LLL12b, (10 mg/kg) by daily intraperitoneal for 7 days. FIG. 9B shows representative peak clinical scores comparing results obtained from the DMSO and LLL12b treatment groups. FIG. 9C shows area under the curve comparing results obtained from the DMSO and LLL12b treatment groups. The data show that therapeutic administration of LLL12b significantly suppresses EAE development in treated mice. One representative of four independent experiments was shown in FIGS. 9A-9C. The summary of all four independent experiments was shown below in Table 1.

Table 1.

Therapeutic Administration of LLL12b Ameliorated Adoptively Transferred EAE.

| Groups | Number of Mice | Incidence of EAE (%) | Mean peak clinical score | Area under the curve |
|---|---|---|---|---|
| DMSO | 41 | 41/41 (100%) [a] | 2.90 ± 0.20 [b] | 42.90 ± 4.80 [c] |
| LLL12b | 34 | 26/34 (76%) [a] | 2.03 ± 0.27 [b] | 22.12 ± 2.09 [c] |

EAE was induced via adoptive transfer of activated myelin-specific CD4 T cells from Vα2.3/Vβ8.2 TCR transgenic mice into B10.PL mice. LLL12b or DNSO (vehicle control) was injected i.p. into mice daily for 7 days, starting when 70% of the mice developed clinical EAE. Mice were monitored for clinical signeds of EAE. Assessment of clinical EAE includes the incidence of EAE, the mean peak clinical scores±SEM and the area under the curve. The results of three independent experiments are shown. [a]P<0.01, comparing incidence of EAE in LLL12b group versus DMSO group. [b]P<0.01, comparing mean peak clinical score of LLL12b group versus DMSO group. [c]P<0.05, comparing area under the curve of LLL12b group versus DMSO group.

Figure 10A:
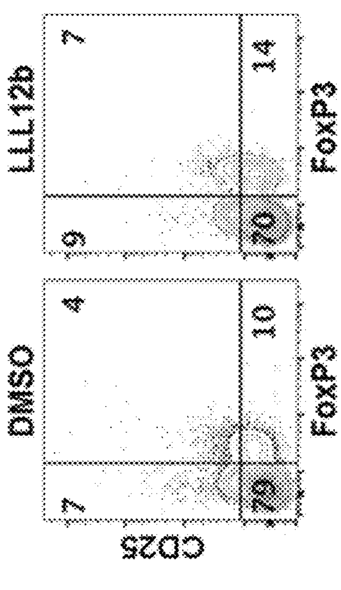
FIGS. 10A-10C show representative data for the effect of treatment with a representative disclosed compound, LLL12b, on Treg development in an adoptively transferred EAE model of MS. Briefly, splenocytes from were isolated from either a LLL12b- or DMSO-treated group as indicated and analysed.
Figure 10B:
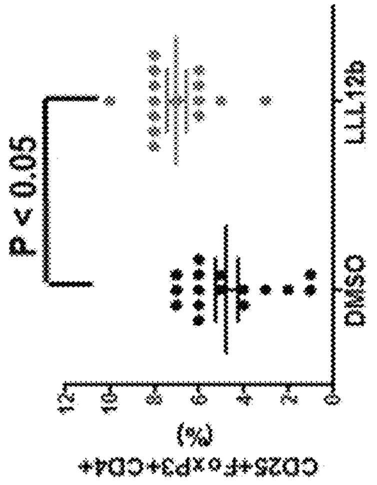
Figure 10C:
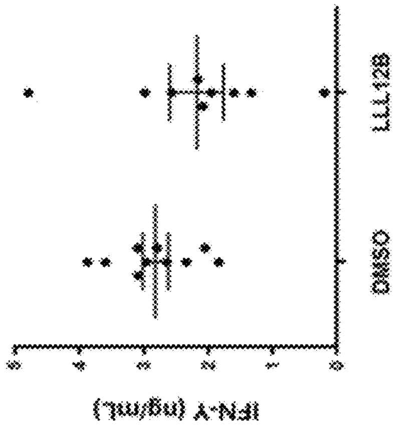

LLL12b treatment suppresses the production of inflammatory cytokines in myelin-specific CD4 T cells and promotes Treg development in vivo. The ex vivo analysis to determine the T effector function of myelin-specific CD4 T cells as well as Treg development in treated mice was carried. FIGS. 10A-10C show representative data for the effect of treatment with a representative disclosed compound. LLL12b, on Treg development in an adoptively transferred EAE model of MS. Briefly, splenocytes from were isolated from either a LLL12b- or DMSO-treated group as indicated and analysed. FIG. 10A shows data for intracellular flow cytometric analysis of CD25+FoxP3+ CD4+ Treg cells. FIG. 10B shows Treg population summary data for each treatment group. FIG. 10C shows data from splenocytes obtained from the LLL12b- or DMSO-treated group as indicated which were activated with MBP Ac1-11 for 3 days followed by determination of IFNγ production by ELISA. The data show a statistically significant increase in the level of Treg cells in LLL12b-treated animals. Moreover, the data show a notable decrease in the production of IFNγ.

Figure 11A:
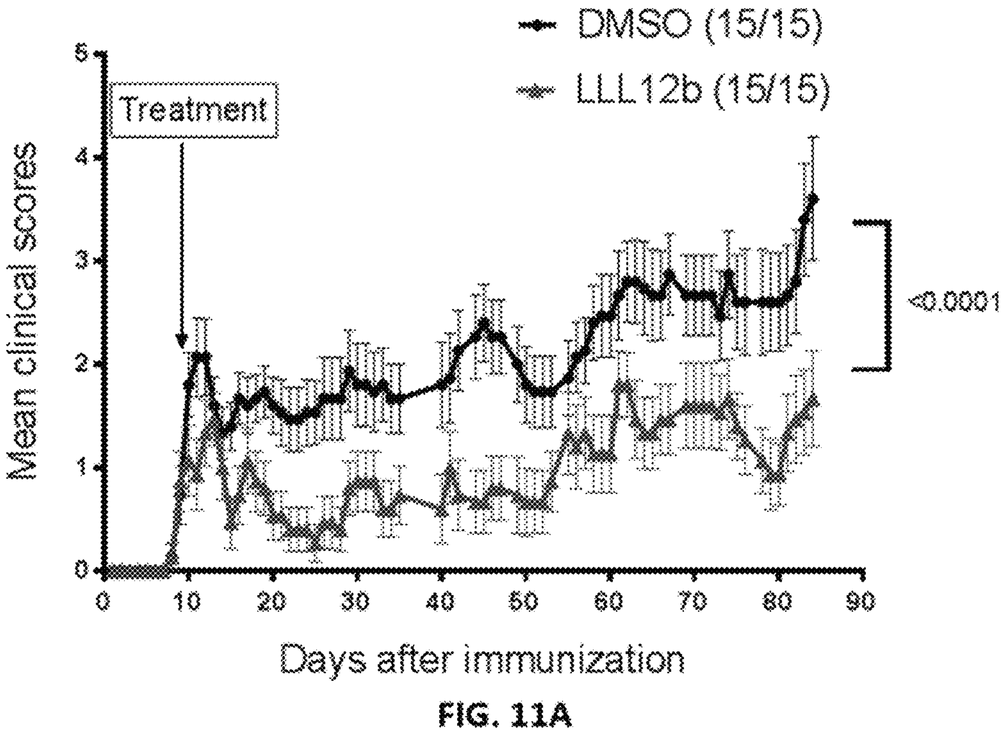
FIGS. 11A-11B show representative data on the effect of a representative disclosed compound, LLL12b, on suppression of acute and relapsing EAE in a relapsing-remitting EAE model of MS. Briefly, naïve SJL mice were immunized with PLP 130-151.
Figure 11B:
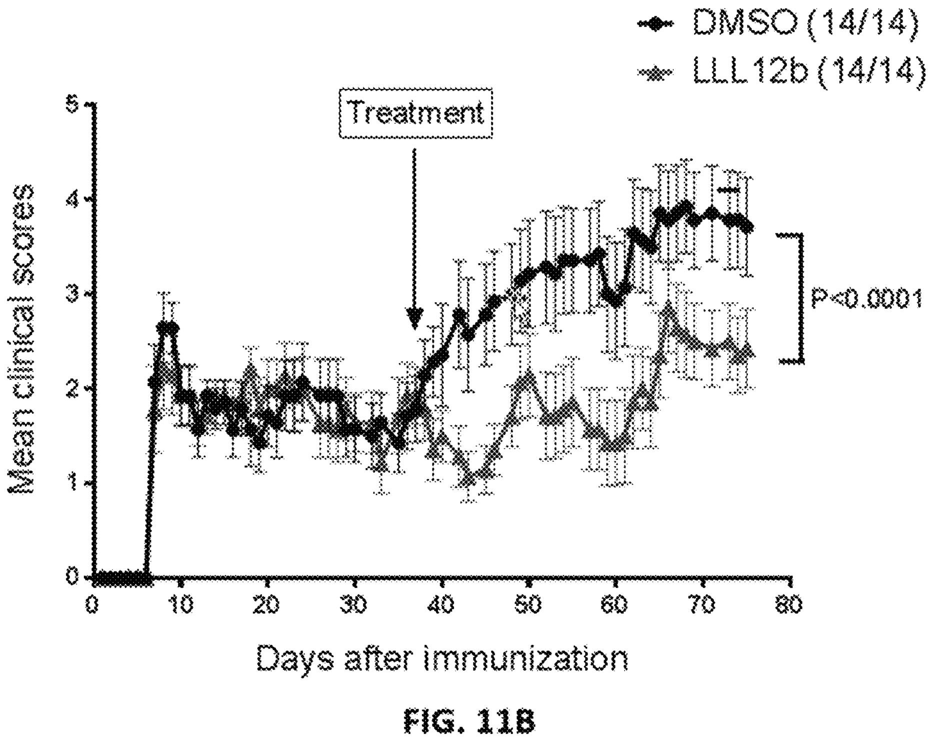

Therapeutic administration of novel prodrug LLL12b significantly suppresses acute and relapsing EAE in relapsing-remitting EAE model of MS in vivo. SJL mice develop relapsing-remitting disease after immunization with PLP 139-151, which resembles human relapsing-remitting MS, the major subtype of MS that affects more than 85% of MS patients. To determine the therapeutic efficacy of prodrug LLL12b in suppressing the development of relapsing-remitting disease, SJL mice were immunized with PLP 139-151, followed by ip injection of 10 mg/ml of LLL12b or vehicle control for 7 days during EAE onset (starting on day 9 after immunization) or during remitting phase (starting on day 36 after immunization). FIGS. 11A-11B show representative data on the effect of a representative disclosed compound, LLL12b, on suppression of acute and relapsing EAE in a relapsing-remitting EAE model of MS. Briefly, naïve SJL mice were immunized with PLP 130-151. FIG. 11A shows the effect of daily injection (days 9-15) of either LLL12b (10 mg/kg) or DMSO as indicated on mean clinical score. During the treatment period, more than half of the mice showed clinical signs of EAE. FIG. 11B shows the effect of daily injection (days 36-42) of either LLL12b (10 mg/kg) or DMSO as indicated on mean clinical score. During the treatment period, EAE mice were in remitting phase. The data show a statistically significant beneficial effect of LL12b treatment on clinical scores in both the acute and remitting phases in this model.

Figure 12A:
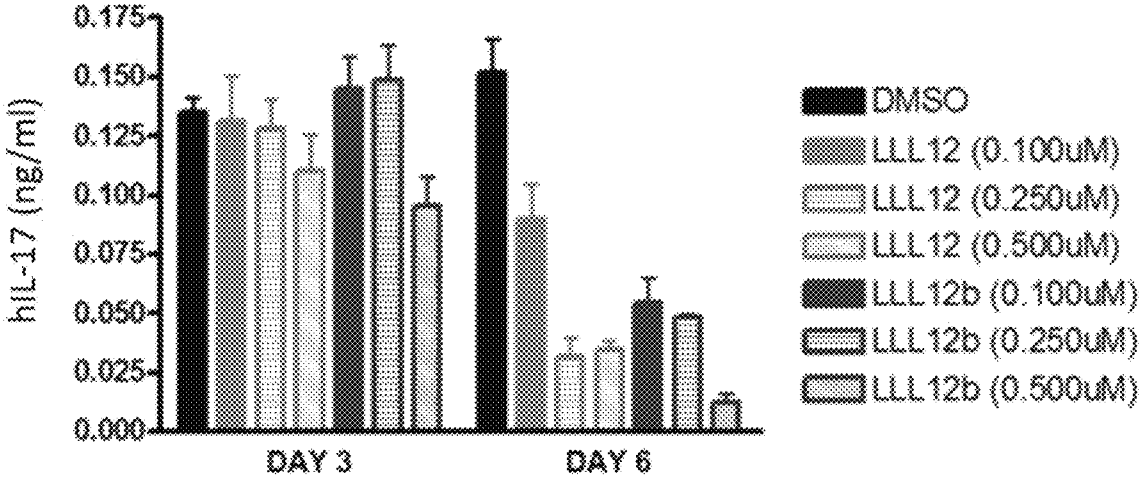
FIGS. 12A-12B show representative data for the effect of a representative disclosed compound, LLL12b, on the production of proinflammatory cytokines in human peripheral blood mononuclear cells (PBMCs). Briefly, PBMCs were isolated from an MS patient and then activated with anti-CD3 for either three or six days as indicated in the figures in the present of different concentrations of LLL12. LLL12b or DMSO as indicated in the figures.
Figure 12B:
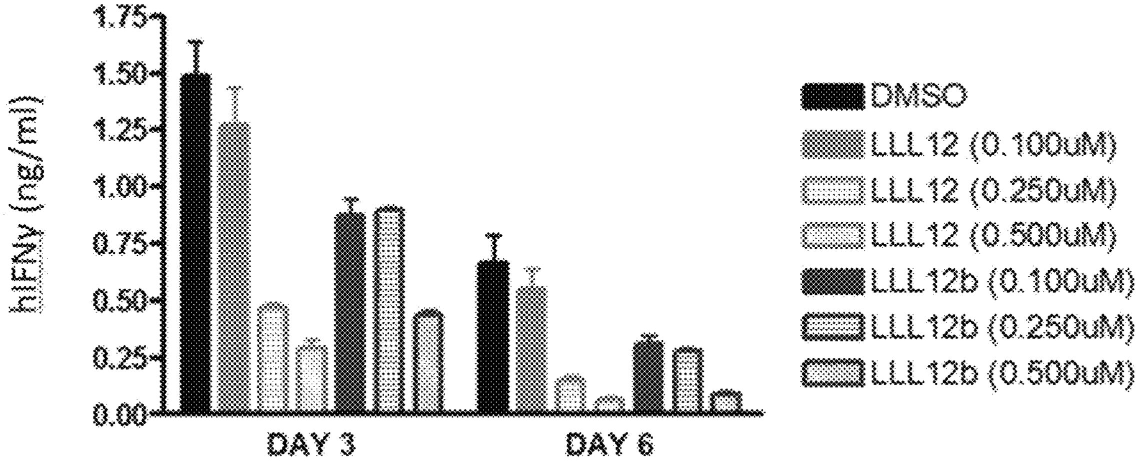

LLL12 and LLL12b suppress IL-17 production in PBMCs from MS patients. To determine the potential efficacy of novel STAT3 inhibitors on suppressing effector function of human CD4 T effector cells, hPBMCs from MS patients (frozen samples) were activated with anti-CD3 in the presence of different concentrations of LLL12, LLL12b or DMSO. FIGS. 12A-12B show representative data for the effect of a representative disclosed compound, LLL12b, on the production of proinflammatory cytokines in human peripheral blood mononuclear cells (PBMCs). Briefly, PBMCs were isolated from an MS patient and then activated with anti-CD3 for either three or six days as indicated in the figures in the present of different concentrations of LLL12, LLL12b or DMSO as indicated in the figures. FIG. 12A shows the effect on IL-17 production under the indicated conditions as determined by ELISA. FIG. 12B shows the effect on IFNγ production under the indicated conditions as determined by ELISA.

Figure 13A:
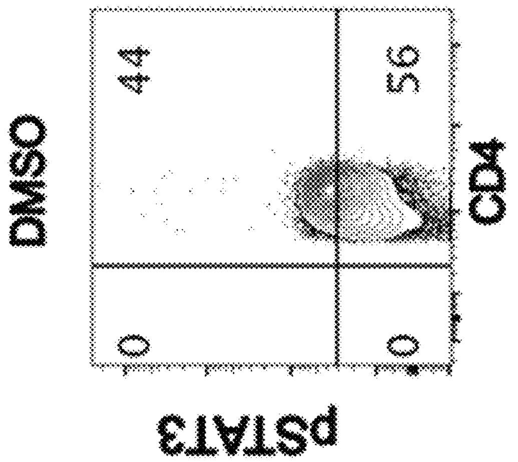
FIGS. 13A-13C show representative data for the effect of LLL12b treatment on the phosphorylation status of STAT3 in CD4 T-cells obtained from MS patients. Briefly, PBMCs from treatment-naïve MS patients were activated with αhCD3 plus rhIL-6 for 30 minutes, in the presence of 0.25 μM of LLL12b or vehicle control (DMSO). pSTAT3 was determined by phospho flow cytometry. Cells were gated on CD4+ cells.
Figure 13B:
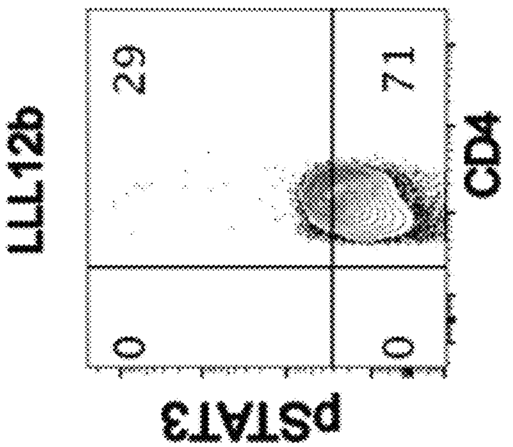
Figure 13C:
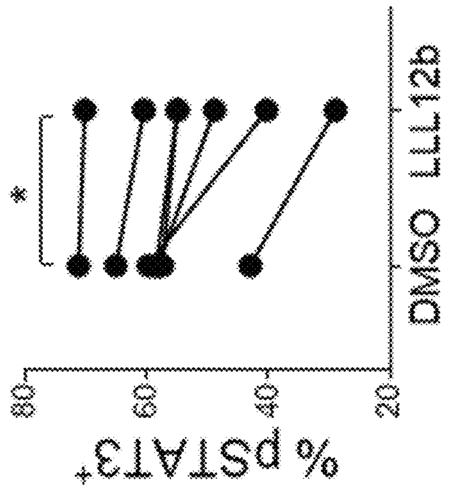

LLL12b inhibits the phosphorylation of STAT3 in CD4 T cells from MS patients. To determine whether LLL12b suppresses the phosphorylation of STAT3 in human CD4 T cells, PBMCs from 6 treatment-naïve MS patients were activated with αhCD3 plus rhIL-6 for 30 minutes, in the presence of 0.25 μM of LLL12b or vehicle control (DMSO). pSTAT3 was determined by phospho flow cytometry. The data show that LLL12b significantly suppresses pSTAT3 expression in CD4 T cells from MS patients (see FIGS. 13A-13C).

Figures 14A, 14B, 14C, 14D, 14E, 14F, 14G:
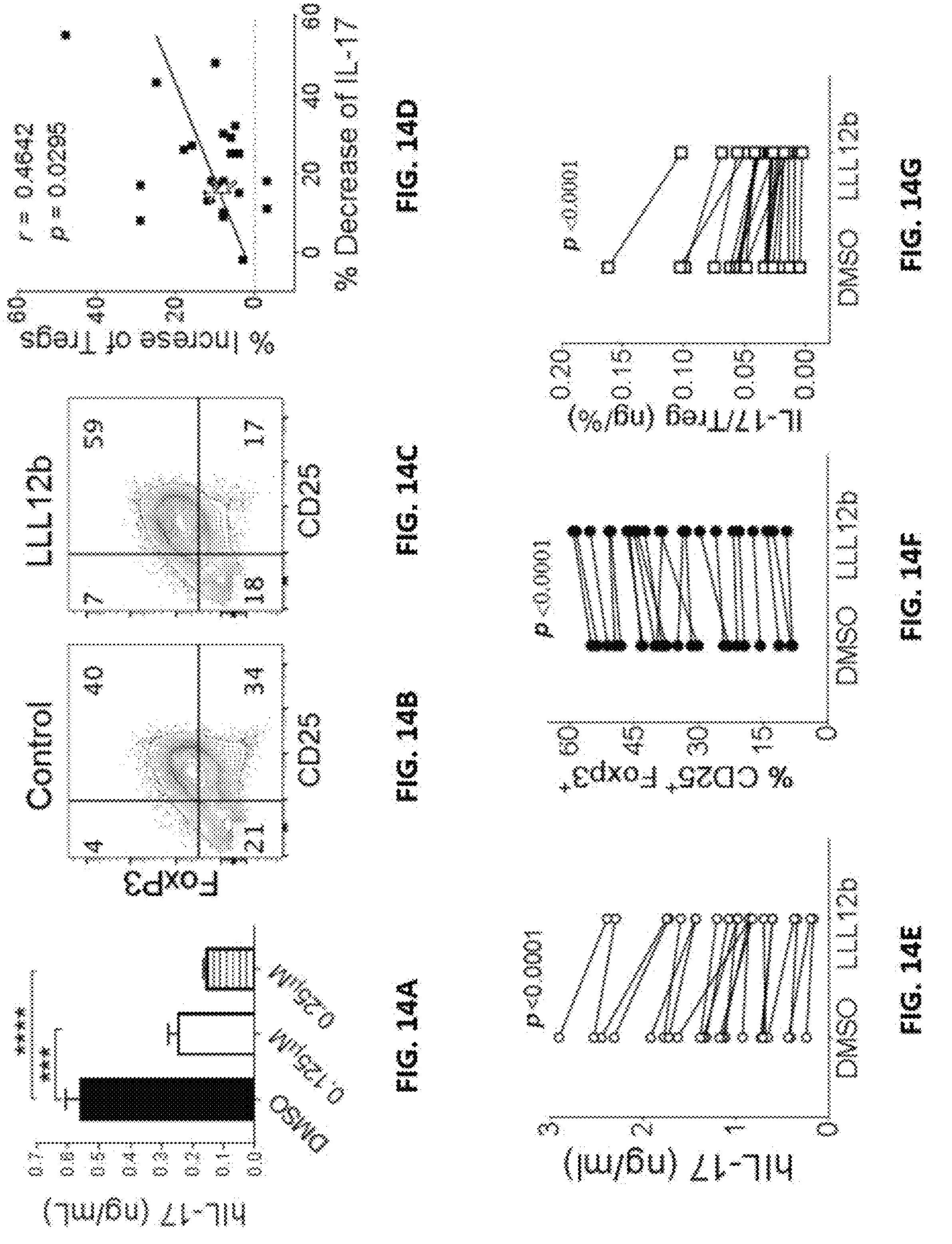
FIGS. 14A-14M show representative data for LLL12b suppression of human Th17 development and promotion of Treg development in CD4 T-cells from MS patients.
Figure 14H:
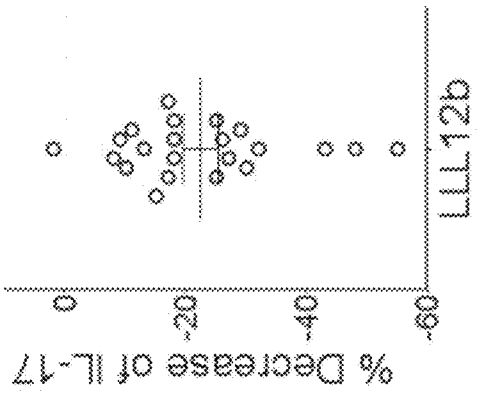
Figure 14I:
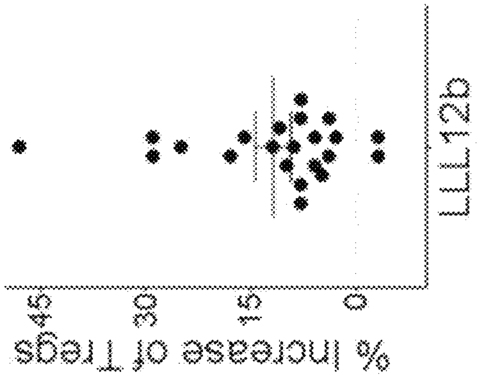

LLL12b reduces Teff/Treg ratio by suppressing human Th17 development and promoting Treg development of CD4 T cells from MS patients. Teff/Treg balance is critical for the normal function of the human immune system and increased Teff/Treg ratio favors autoimmunity. As IL-6/STAT3 signaling pathway is critical for the highly encephalitogenic Th17 cells while blocks the development of inducible Tregs (iTregs), we hypothesize that novel small molecule STAT3 inhibitor LLL12b will reduces Teff/Treg ratio by suppressing Th17 development and/or prompting iTreg development. Therefore, we determined the effects of LLL12b on IL-17 production and iTreg development of CD4 T cells from 22 treatment-naïve MS patients (FIGS. 14A-14M). Human PBMCs from 22 treatment-naïve MS patients were activated with αhCD3 for 3 days, in the presence of different concentrations of LLL12b or vehicle control (DMSO), IL-17 production in supernatants was determined by ELISA. As the myelin-reactive CD4 T cells in MS patients are predominantly from the memory T-cell compartment, we activated human PBMCs with αhCD3 to specifically activate effector/memory CD4 T cells. LLL12b suppressed hIL-17 production at both 0.125 μM and 0.25 μM (FIG. 14A). The hIL-17 production in effector/memory CD4 T cells from 22 treatment-naïve MS patients treated with 0.125 μM of LLL12b or DMSO were summarized in Fig B-D. Our data show that LLL12b significantly suppressed IL-17 production in effector/memory human CD4 T cells from MS patients, suggesting LLL12b has the capacity to inhibit the effector function of effector/memory CD4 T cells from MS patients.

Meanwhile, we determined the extent to which LLL12b promotes the development of iTregs of CD4 T cells from MS patients (FIGS. 14B-14C, 14F, 14I, and 14L). PBMCs from 22 treatment-naïve MS patients were activated with αhCD3/CD28 for 3 days, in the presence of TGFβ, IL-2 and trans-retinoic acid (iTreg differentiating condition). The percentage of iTregs from naïve CD4+CD45RA+ T cells in one MS patient is shown in FIGS. 14B and 14C. After 72 h of culture under iTreg differentiating condition, the total number of CD25+FoxP3+ iTregs in the CD4+CD45RA+ population increased from 40% in control group to 59% in the group treated with LLL12b. The iTregs in 22 treatment-naïve MS patients treated with 0.125 μM of LLL12b were summarized in FIGS. 14F, 14I, and 14L. The data show that LLL12b significantly promotes iTreg development of CD4 T cells from MS patients, demonstrating that LLL12b has the capacity to promote human Treg development.

Figure 14J:
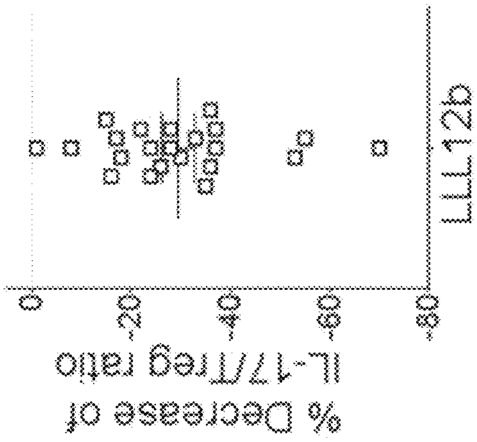
Figure 14K:
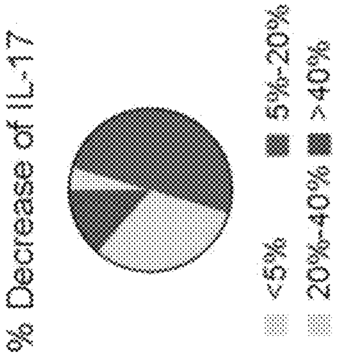
Figure 14L:
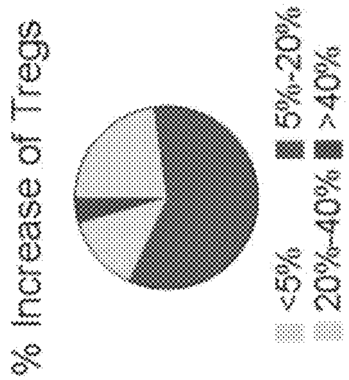
Figure 14M:
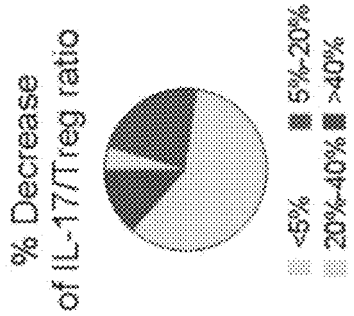
Figure 15A:
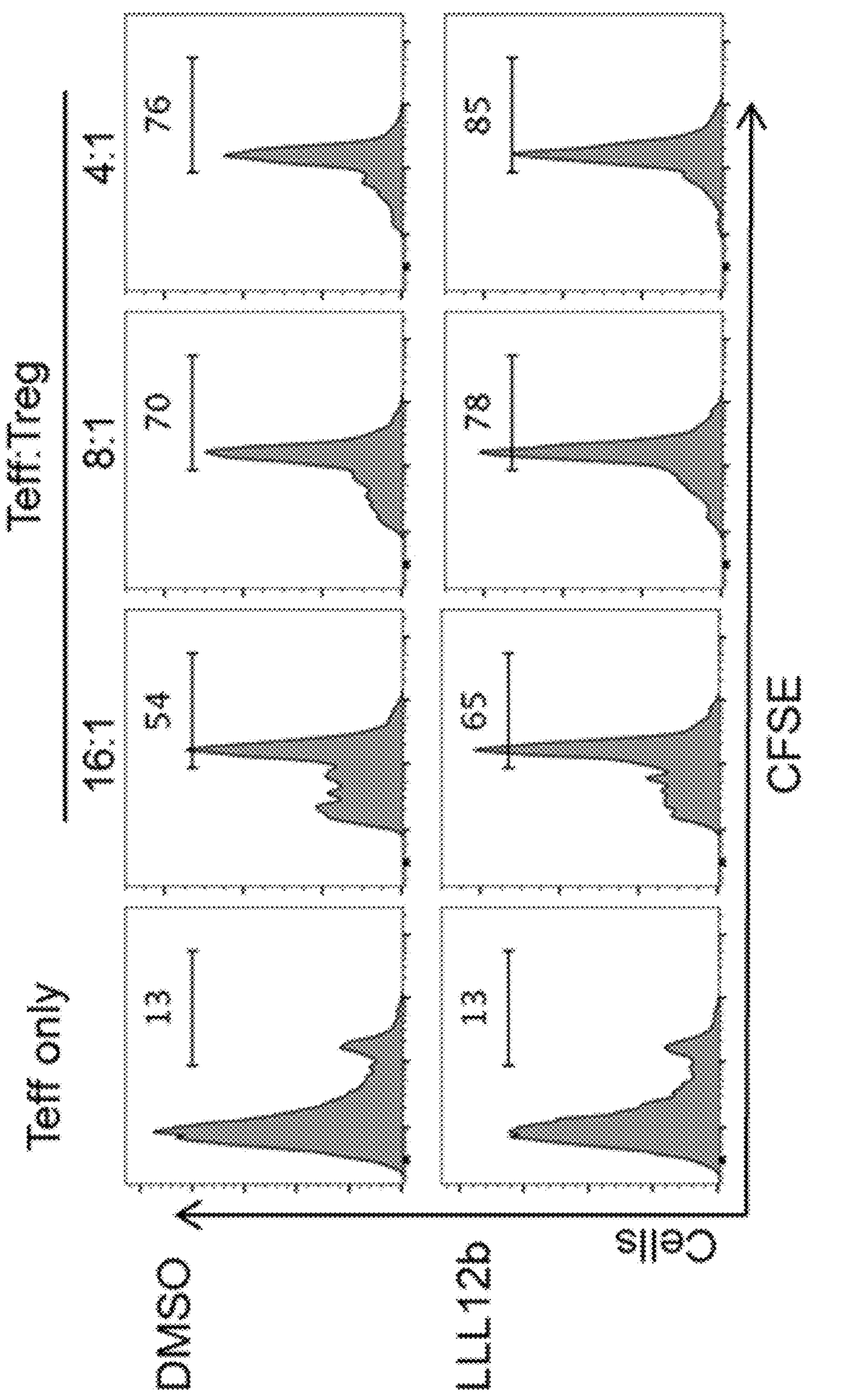
FIGS. 15A-15C show representative data for LLL12b enhancement of Treg-mediated suppression on Teff cells obtained from MS patients. PBMCs were obtained from three treatment-naïve MS patients and were activated with αhCD3/CD28 plus rhTGFβ, rhIL-2 and RA for 3 days to generate Tregs. Meanwhile, PBMCs from the same three MS patients were labeled with CFSE and cultured with 0.25 μM of LLL12b or DMSO for 1-2 hours. The LLL12b or DMSO treated CFSE-CD4 T cells were then mixed with Tregs generated from the same patient at different ratios and activated with αhCD3 for 5 days. Proliferation of Teff cells was determined by flow cytometric analysis of CFSE on CD4 T cells. Cells were gated on CD4+ cells.
Figure 15B:
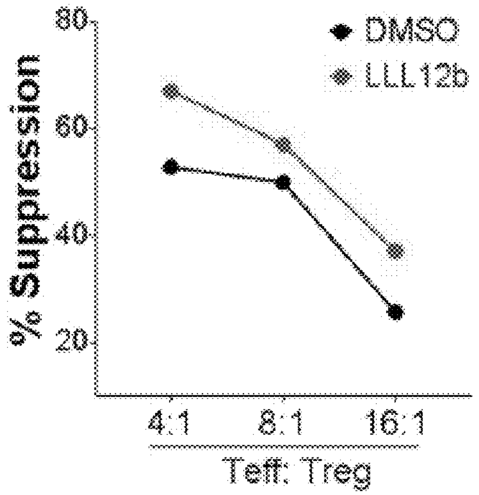
Figure 15C:
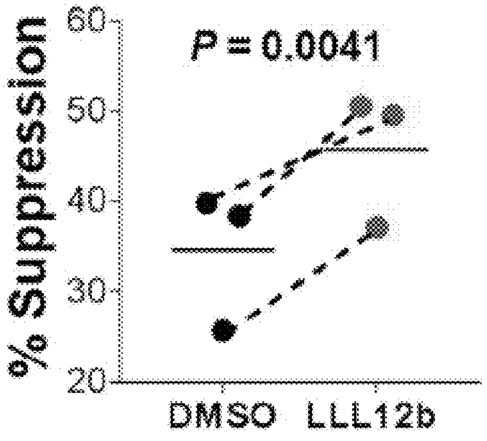
Figure 16A:
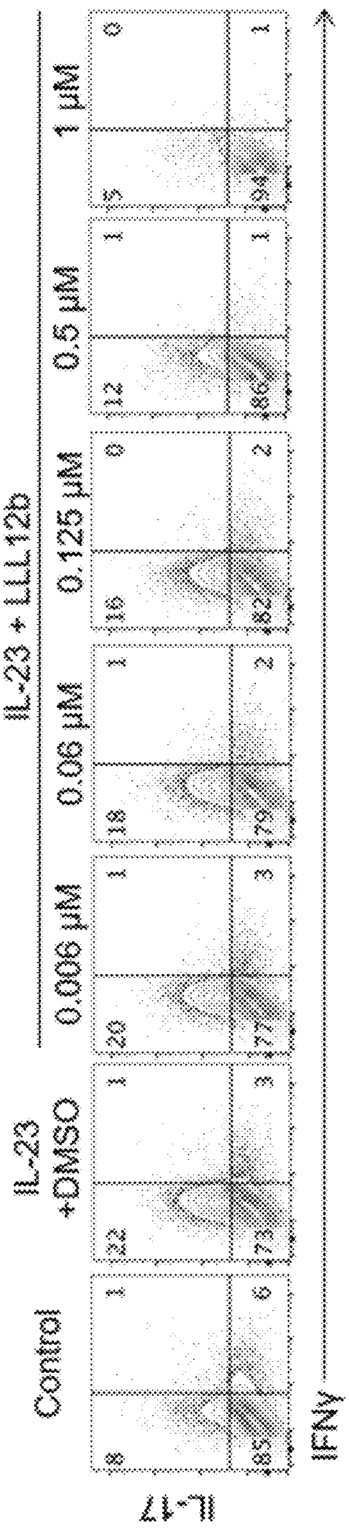
FIGS. 16A-16C show representative data for LLL12b inhibition of IL-23-induced IL-17 production in myelin specific CDT T cells. Briefly, SJL mice were immunized with PLP 139-151. Splenocytes were isolated on day 20 after immunization and activated with PLP 139-151 with our without IL-23 for 3 days, in the presence of different concentrations of LLL12b or DMSO (vehicle control).
Figure 16B:
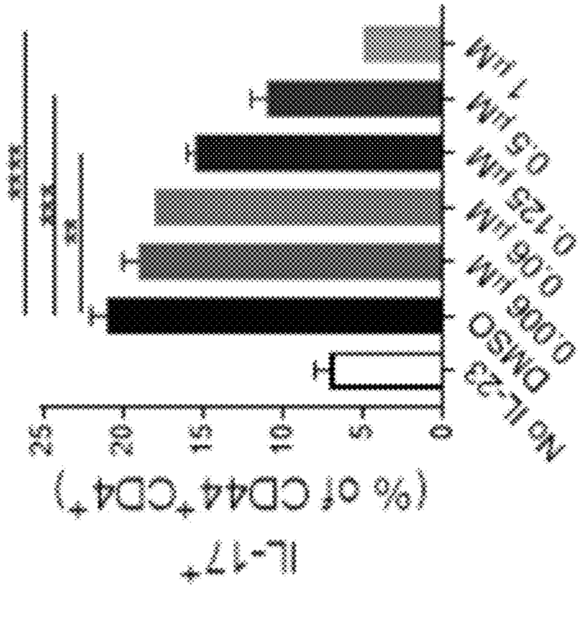
Figure 16C:
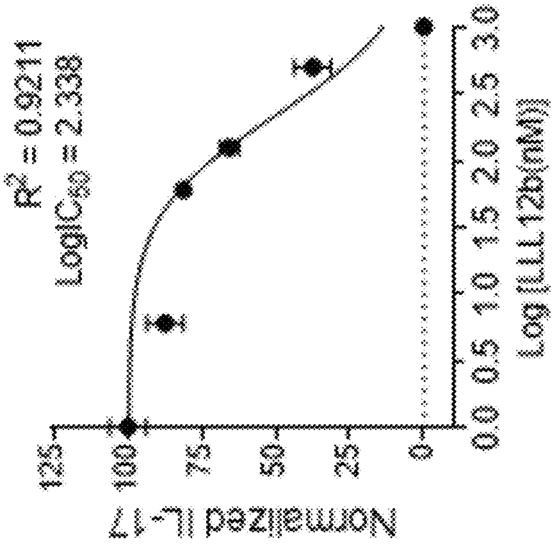
Figure 17A:
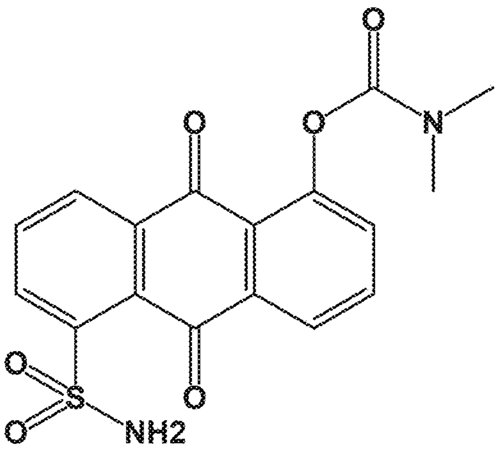
FIG. 17 shows the structures of the compounds evaluated in the DeepAtom model study.
Figure 17A:
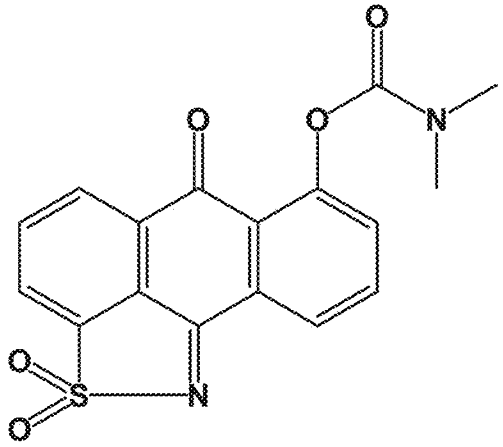
Figure 17A:
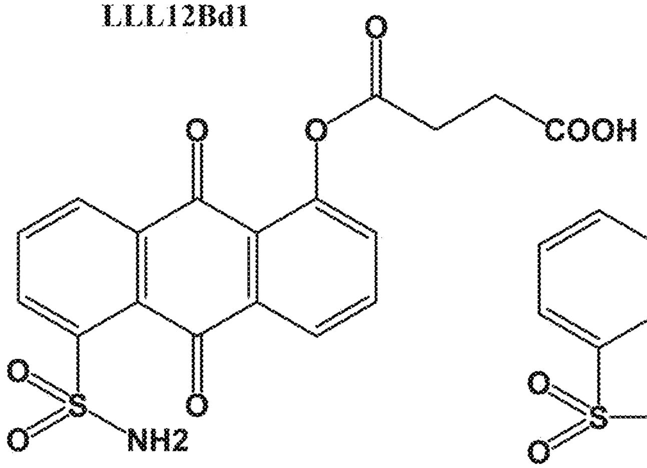
Figure 17A:
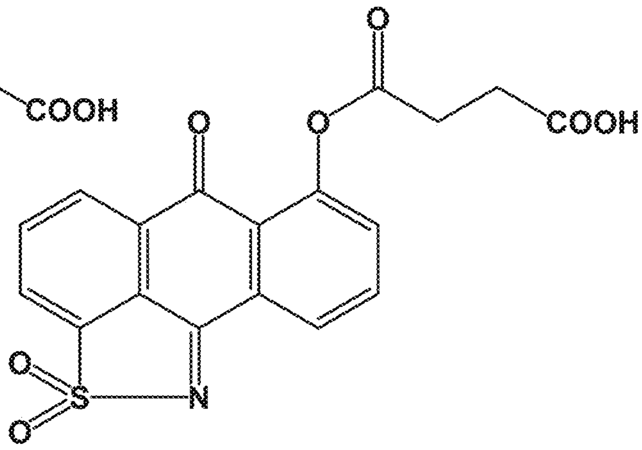
Figure 17A:
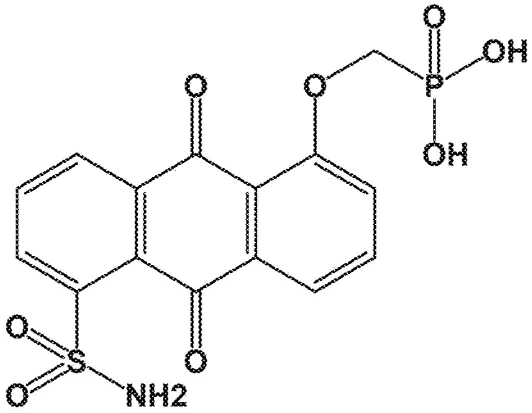
Figure 17A:
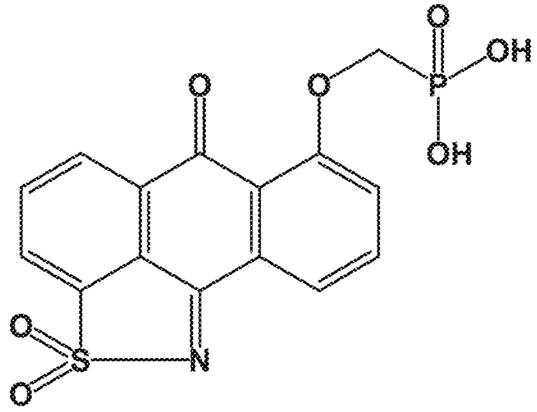
Figure 17B:
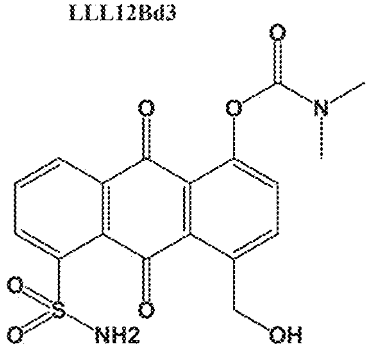
Figure 17B:
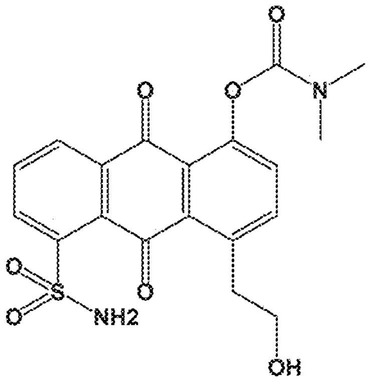
Figure 17B:
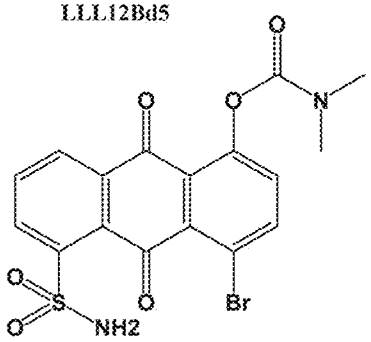
Figure 17B:
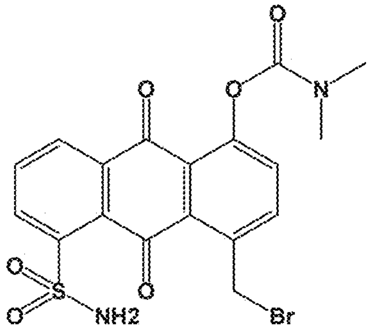
Figure 17B:
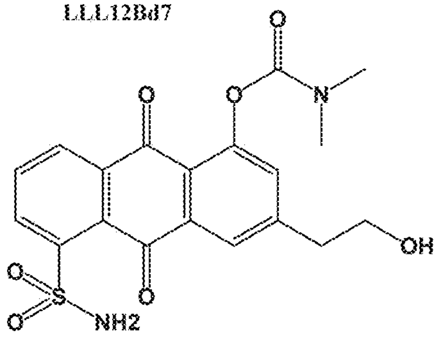
Figure 17B:
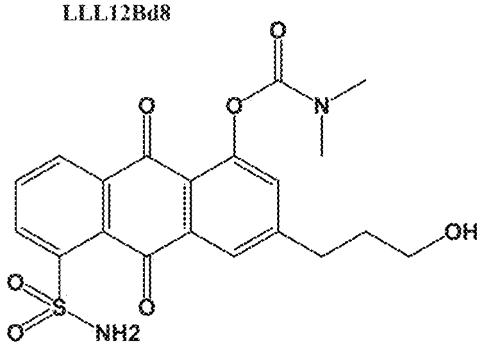
Figure 17B:
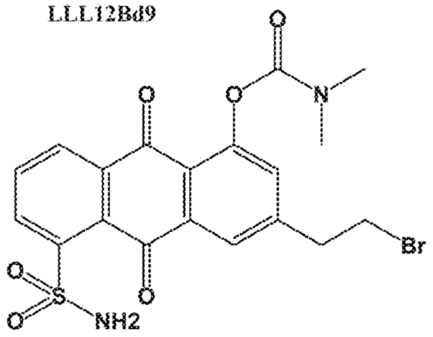
Figure 17B:
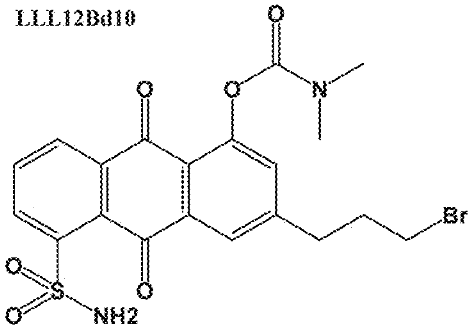

To determine whether LLL12b treatment decreases Th17/Treg ratio in CD4 T cells from MS patients, the IL-17/Treg ratio of all 22 treatment-naïve MS patients treated with LLL12b was calculated and compared with those treated with DMSO (FIGS. 14G, 14J, and 14M). The data in Table 2 show the patient numbers in different ranges of percentage decrease of IL-17, percentage increase of iTregs or percentage decrease of IL-17/iTreg of 22 treatment-naïve MS patients treated with LLL12b compared to DMSO treatment.

The data show that IL-17/Treg ratio is significantly lower in LLL12b treated group compared to DMSO treated group (FIG. 14G). Moreover, there was a positive correlation between the percent decrease of IL-17 and the percent increase of iTregs, suggesting that the increase of iTreg development by LLL12b treatment contributes to the suppression of IL-17 production by effector/memory CD4 T cells from MS patients.

TABLE 2

| | % Decrease of IL-17 | % Increase of iTregs | % Decrease of IL-17/iTreg ratio |
|---|---|---|---|
| <5% | 1 | 5 | 1 |
| 5-20% | 11 | 13 | 5 |
| 20-40% | 7 | 3 | 13 |
| >40% | 3 | 1 | 3 |

LLL12b enhances Treg mediated suppression on Teff cells from MS patients. Since Teff cells from MS patients are resistant to Treg mediated suppression and IL-6/STAT3 signaling promotes the resistance of Teff in MS patient, we determined whether LLL12b may enhance the Treg-mediated suppression on Teff from MS patients using CFSE-based suppression assay. PBMCs from three treatment-naïve MS patients were labeled with CFSE and cultured with 0.25 μM of LLL12b or DMSO for 1-2 hrs. Then the CFSE-CD4 T cells were mixed with iTregs differentiated from the same patient at different ratio, and activated with αhCD3 for 5 days. Our data show that iTregs suppress the proliferation of Teff cells from MS patients in a dose-dependent manner (FIG. 3A, upper panel; FIG. 3B black line). More importantly, LLL12b treatment increases the suppression efficiency (% suppression) of Tregs on Teff proliferation in all three ratios, compared to DMSO treatment (FIG. 3B, lower panel; FIG. 3B red line). The suppression efficiency in LLL12b treated group from 3 treatment-naïve MS patients' was compared to DMSO group and it showed that LLL12b significantly increased Treg mediated suppression on Teff cells from MS patients (FIG. 3C).

Modeling Studies. Several compounds falling under the structures described herein were evaluated using the DeepAtom model (Rezaei et al., EEE/ACM Trans Comput Biol Bioinform 2022 January-February; 19(1):407-417. doi: 10.1109/TCBB.2020.3046945. Epub 2022 Feb. 3). In particular, several compounds were evaluated using the DeepAtom deep learning STAT3/analog binding affinity model and compared to LLL12B. Structures of the compounds evaluated are provided in FIG. 17.

The results of the modeling studies are provided in the Table 3 below. The more negative the value in Kcal/mol, the more potent the compound is with respect to STAT3/analog binding affinity and, ultimately, inhibition of STAT3. The data in Table 3 shows that all the analogs evaluated are comparable or better than LLL12B with respect to STAT3 affinity and inhibition.

TABLE 3

| Inhibitors | DeepAtom Score (Kcal/mol) |
|---|---|
| LLL12 | −7.7 |
| LLL12B | −6.1 |
| LLL12Ba | −5.7 |
| LLL12Bad1 | −6.5 |
| LLL12Bad2 | −5.8 |
| LLLBd | −7.3 |
| LLLBd | −7.5 |
| LLL12B43 | −6.4 |
| LLL12Bd4 | −5.6 |
| LLL12Bd5 | −6.2 |
| LLL12Bd6 | −5.8 |
| LLLBd | −6.3 |
| LLL12Bd8 | −6.0 |
| LLL12Bd9 | −6.8 |
| LLL12Bd10 | −7.0 |

Based on the data presented in Table 3, the compounds described herein can be useful as STAT3 inhibitors for the treatment of inflammatory disorder, including multiple sclerosis, or a disorder of uncontrolled cellular proliferation, such as a cancer.

Figure 18A:
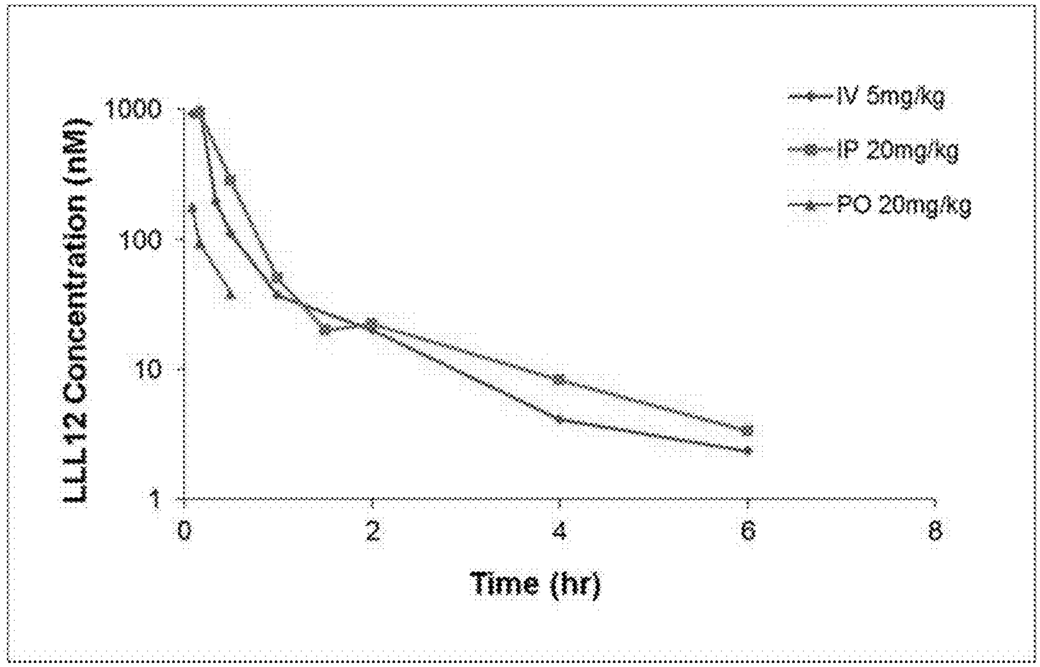
FIGS. 18A-18B show overlaid semi logarithmic (A) and linear (B) plots of concentration-time profiles of LLL12 in mice by IV, IP and oral routes. The IP 5 min time point was removed.
Figure 18B:
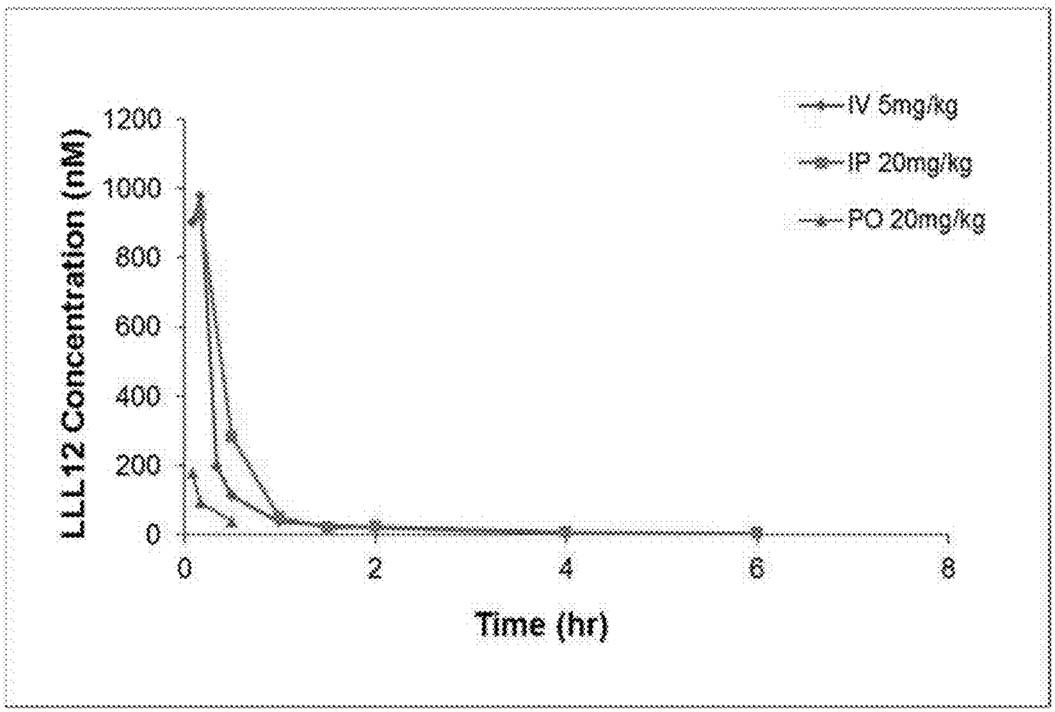

Pharmacokinetic Studies. LLL12B is the carbamate prodrug of the phenol LLL12. As shown in FIGS. 18*a* and 18*b* and Table 4, LLL12 has poor PK properties with Tmax of 5-10 minutes but cleared in about 30 minutes for PO and 60 minutes for IV and IP.

TABLE 4

The area-under-curve and relative bioavailability of LLL12 in mice dosed IV, IP and PO

| | | LLL12 | | |
|---|---|---|---|---|
| PK parameters | Unit ↓ (Dosage→) | IV 5 mg/kg | PO 20 mg/kg | IP 20 mg/kg |
| Tmax | hr | 0.167 | 0.083 | 0.167 |
| Cmax | nM | 978 | 176 | 922 |
| AUCall | nM*hr | 373 | 40.7 | 431 |
| AUC inf_obs | nM*hr | 377 | NA | 438 |
| F | % | 100 | 2.73 | 29.1 |

Figure 19A:
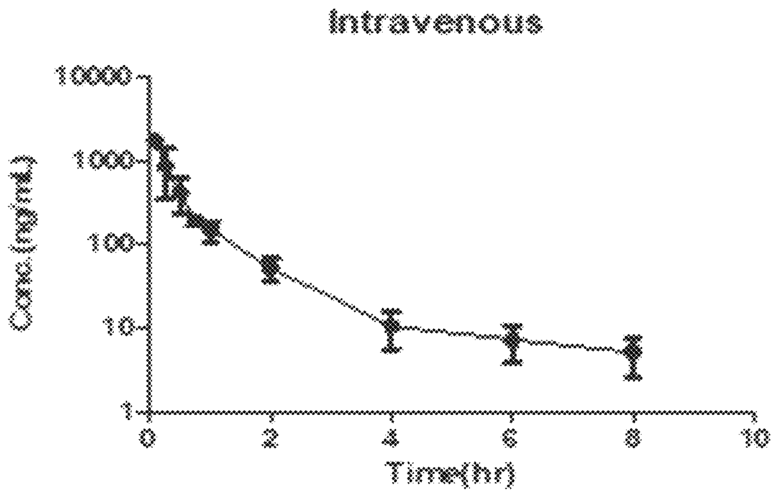
FIGS. 19A-19B show the linear plots of concentration-time profiles of LLL12B in mice by IV and oral routes.
Figure 19B:
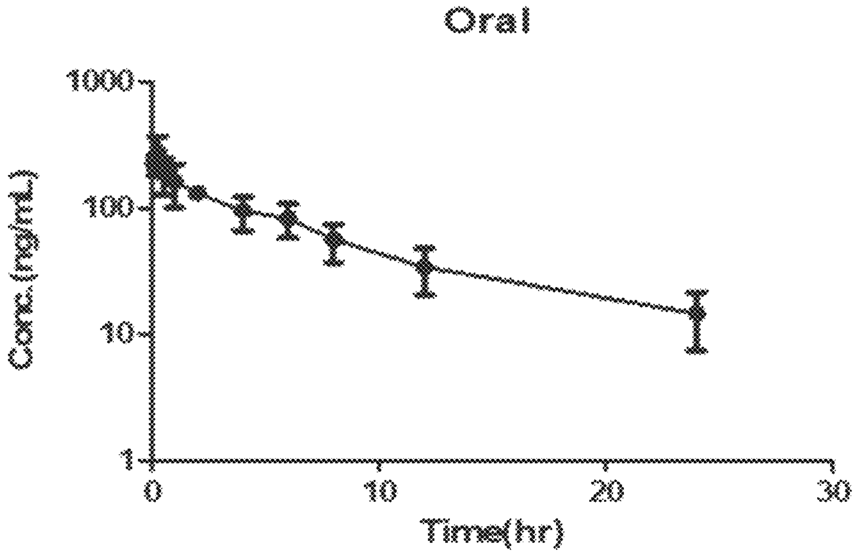

Conversely, LLL12B has sustained effective concentration for IV about 4 hours and for PO about 8 hours with much better Cmax and AUC values, as shown in FIGS. 19*a* and 19*b* and Table 5.

TABLE 5

The area-under-curve and relative bioavailability of LLL12B in mice dosed IV and PO

| Parameters | Intravenous 2 mg/kg | Oral 8 mg/kg |
|---|---|---|
| Co/Cmax (ng/mL) | 2879.87 ± 934.57 | 277.75 ± 92.96 |
| Tmax (hr) | — | 0.19 ± 0.09 |
| $AUC_{0-t}$(hr*ng/mL) | 892.29 ± 130.87 | 1356.77 ± 395.87 |
| t1/2 (hr) | 3.88 ± 0.45 | 7.68 ± 1.91 |
| Vd (L/kg) | 12.43 ± 2.89 | |
| Cl (L/hr/kg) | 2.19 ± 0.27 | |
| F (%) | 38.01% | |

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

The invention claimed is:

1. A method for ameliorating or alleviating cancer in a mammal comprising the step of administering to the mammal a therapeutically effective amount of at least one compound having a structure represented by a formula,

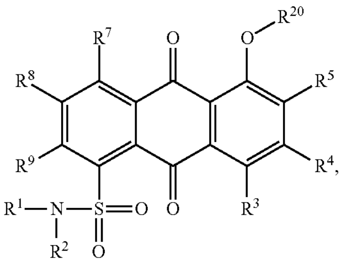

wherein each of $R^1$ and $R^2$ is independently selected from hydrogen and C1-C6 alkyl;

wherein each of $R^3$, $R^4$, $R^5$, $R^7$, $R^8$, and $R^9$ is independently selected from hydrogen, C1-C6 alkyl, C1-C6 alkoxy, halogen, —$NO_2$, —$NH_2$, and —OH; and wherein $R^{20}$ is selected from —C(O)—O—(C1-C6 alkylene), —C(O)—(C1-C6 alkylene), —C(O)—(C1-C6 alkylene)-C(O)OH, —C(O)—$NR^{21}R^{22}$, and —(C1-C6 alkylene)-$PO_3H_2$;

wherein each of $R^{21}$ and $R^{22}$ is independently selected from hydrogen and C1-C6 alkyl;

or a pharmaceutically acceptable salt thereof.

2. The method of claim 1, wherein the cancer is selected the group consisting of breast cancer, renal cancer, gastric cancer, colorectal cancer, multiple myeloma, leukemia, lymphoma, cutaneous T-cell lymphoma, Hodgkin's disease, and a solid tumor.

3. The method of claim 1, wherein the compound has a structure represented by a formula:

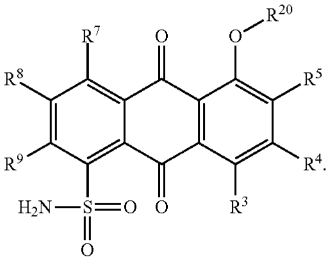

4. The method of claim 1, wherein the compound has a structure represented by a formula:

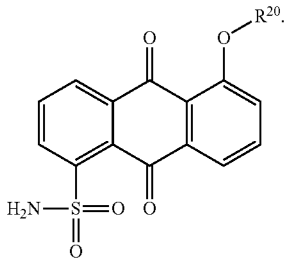

5. The method of claim 1, wherein $R^{20}$ is selected from —C(O)—(C1-C6 alkylene)-C(O)OH, —C(O)—$NR^{21}R^{22}$, and —(C1-C6 alkylene)-$PO_3H_2$; and wherein each of $R^{21}$ and $R^{22}$ is independently selected from hydrogen and C1-C6 alkyl.

6. The method of claim 1, wherein $R^{20}$ is selected from —C(O)—(C1-C6 alkylene)-C(O)OH, —C(O)—$NR^{21}R^{22}$, and —(C1-C6 alkylene)-$PO_3H_2$; and wherein each of $R^{21}$ and $R^{22}$ is independently selected from hydrogen and methyl.

7. The method of claim 1, wherein $R^{20}$ is selected from —C(O)—$(CH_2)_2$—C(O)OH, —C(O)—$NH_2$, and —$(CH_2)$—$PO_3H_2$.

8. The method of claim 1, wherein the compound has a structure represented by a formula:

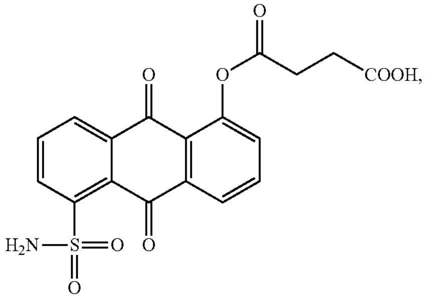

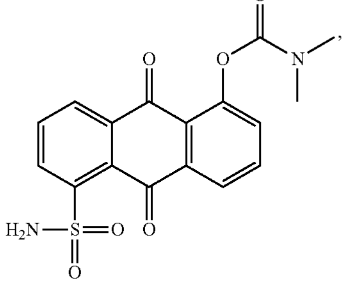

or

-continued

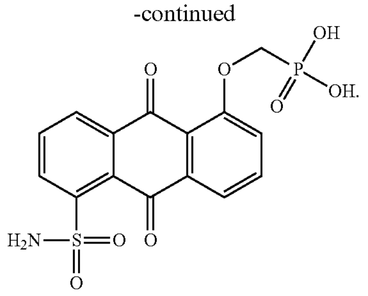

9. The method of claim 1, wherein the compound has a structure represented by a formula:

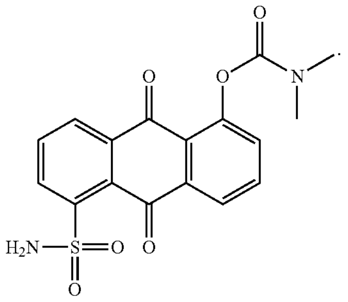 [SMILES: CN(C)C(=O)Oc1cccc2c1C(=O)c1cccc(S(N)(=O)=O)c1C2=O]

10. A method for ameliorating or alleviating cancer in a mammal comprising the step of administering to the mammal a therapeutically effective amount of at least one compound having a structure represented by a formula:

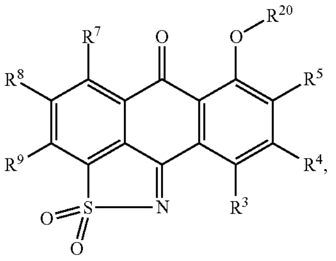

wherein each of $R^3$, $R^4$, $R^5$, $R^7$, $R^8$, and $R^9$ is independently selected from hydrogen, C1-C6 alkyl, C1-C6 alkoxy, halogen, —$NO_2$, —$NH_2$, and —OH; and wherein $R^{20}$ is selected from —C(O)—O—(C1-C6 alkylene), —C(O)—(C1-C6 alkylene), —C(O)—(C1-C6 alkylene)-C(O)OH, —C(O)—$NR^{21}R^{22}$, and —(C1-C6 alkylene)-$PO_3H_2$;

wherein each of $R^{21}$ and $R^{22}$ is independently selected from hydrogen and C1-C6 alkyl;

or a pharmaceutically acceptable salt thereof.

11. The method of claim 10, wherein the cancer is selected the group consisting of breast cancer, renal cancer, gastric cancer, colorectal cancer, multiple myeloma, leukemia, lymphoma, cutaneous T-cell lymphoma, Hodgkin's disease, and a solid tumor.

12. The method of claim 10, wherein the compound has a structure represented by a formula:

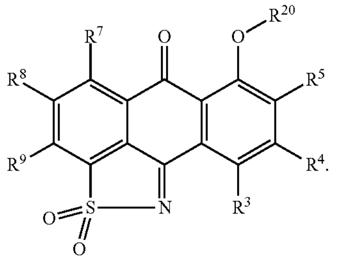

13. The method of claim 10, wherein the compound has a structure represented by a formula:

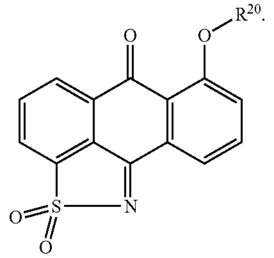

14. The method of claim 10, wherein $R^{20}$ is —C(O)—(C1-C6 alkylene)-C(O)OH, C(O)—$NR^{21}R^{22}$, and —(C1-C6 alkylene)-$PO_3H_2$; and wherein each of $R^{21}$ and $R^{22}$ is independently selected from hydrogen and C1-C6 alkyl.

15. The method of claim 10, wherein $R^{20}$ is —C(O)—(C1-C6 alkylene)-C(O)OH, —C(O)—$NR^{21}R^{22}$, and —(C1-C6 alkylene)-$PO_3H_2$; and wherein each of $R^{21}$ and $R^{22}$ is independently selected from hydrogen and methyl.

16. The method of claim 10, wherein $R^{20}$ is selected from —C(O)—$(CH_2)_2$—C(O)OH, —C(O)—$NH_2$, and —$(CH_2)$—$PO_3H_2$.

17. The method of claim 10, wherein the compound has a structure represented by a formula:

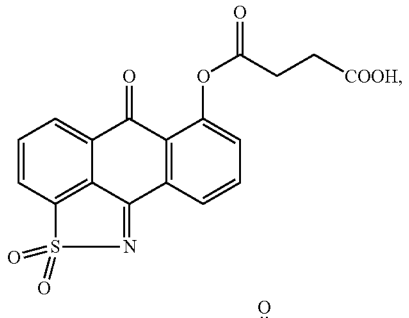

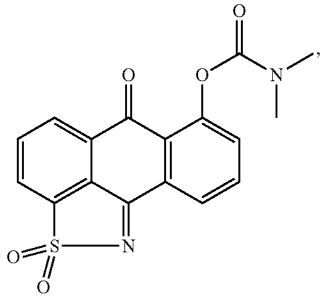

or

-continued

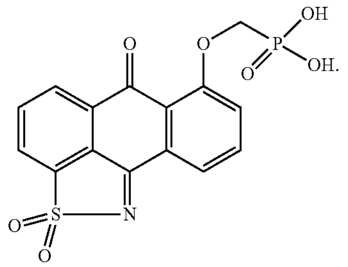

18. The method of claim 10, wherein the compound has a structure represented by a formula:

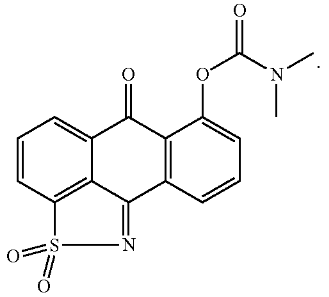 [SMILES: CN(C)C(=O)Oc1cccc2c1C(=O)c1cccc3c1C2=NS3(=O)=O]

19. A method for inhibiting STAT3 in a mammal comprising the step of administering to the mammal a therapeutically effective amount of at least one compound having a structure represented by a formula,

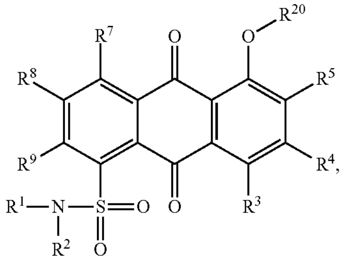

wherein each of $R^1$ and $R^2$ is independently selected from hydrogen and C1-C6 alkyl;

wherein each of $R^3$, $R^4$, $R^5$, $R^7$, $R^8$, and $R^9$ is independently selected from hydrogen, C1-C6 alkyl, C1-C6 alkoxy, halogen, —$NO_2$, —$NH_2$, and —OH; and wherein $R^{20}$ is selected from —C(O)—O—(C1-C6 alkylene), —C(O)—(C1-C6 alkylene), —C(O)—(C1-C6 alkylene)-C(O)OH, —C(O)—$NR^{21}R^{22}$, and —(C1-C6 alkylene)-$PO_3H_2$;

wherein each of $R^{21}$ and $R^{22}$ is independently selected from hydrogen and C1-C6 alkyl;

or a pharmaceutically acceptable salt thereof.

* * * * *